US012649738B2

(12) United States Patent
Szabó et al.

(10) Patent No.: US 12,649,738 B2
(45) Date of Patent: Jun. 9, 2026

(54) 1,3-DIHYDRO-2H-PYRROLO[3,4-C]PYRIDINE DERIVATIVES AS $GABA_A$ α5 RECEPTOR MODULATORS

(71) Applicant: Richter Gedeon Nyrt., Budapest (HU)

(72) Inventors: György Szabó, Maglód (HU); Viktor Ilkei, Budapest (HU); Gábor Varró, Alsónémedi (HU); Attila Potor, Pilis (HU); Gábor László Kapus, Pécel (HU)

(73) Assignee: Richter Gedeon Nyrt., Budapest (HU)

( * ) Notice: Subject to any disclaimer, the term of this patent is extended or adjusted under 35 U.S.C. 154(b) by 659 days.

(21) Appl. No.: 17/907,176

(22) PCT Filed: Mar. 25, 2021

(86) PCT No.: PCT/IB2021/052485

§ 371 (c)(1),
(2) Date: Sep. 23, 2022

(87) PCT Pub. No.: WO2021/191837

PCT Pub. Date: Sep. 30, 2021

(65) Prior Publication Data

US 2024/0043418 A1 Feb. 8, 2024

(30) Foreign Application Priority Data

Mar. 26, 2020 (HU) ...................................... 2000112

(51) Int. Cl.

| | |
|---|---|
| ***C07D 471/04*** | (2006.01) |
| ***A61P 25/00*** | (2006.01) |
| ***A61P 25/18*** | (2006.01) |
| ***A61P 25/28*** | (2006.01) |

(52) U.S. Cl.

CPC .................................. *C07D 471/04* (2013.01)

(58) Field of Classification Search

None

See application file for complete search history.

(56) References Cited

U.S. PATENT DOCUMENTS

| | | | |
|---|---|---|---|
| 5,665,733 | A | 9/1997 | Sevrin et al. |
| 2007/0105922 | A1 | 5/2007 | Buettelmann et al. |
| 2016/0102088 | A1 | 4/2016 | Wurster et al. |
| 2017/0057966 | A1 | 3/2017 | Lange et al. |

FOREIGN PATENT DOCUMENTS

| | | | |
|---|---|---|---|
| CN | 102924452 | A | 2/2013 |
| EP | 0433842 | A2 | 6/1991 |
| EP | 3323809 | A1 | 5/2018 |
| WO | WO-1998050385 | A1 | 11/1998 |
| WO | WO-1999067245 | A1 | 12/1999 |
| WO | WO-2002006285 | A1 | 4/2002 |
| WO | WO-2006065215 | A1 | 6/2006 |
| WO | WO-2007018660 | A2 | 2/2007 |
| WO | WO-2007042420 | A1 | 4/2007 |
| WO | WO-2007072092 | A2 | 6/2007 |
| WO | WO-2007140174 | A2 | 12/2007 |
| WO | WO-2008050167 | A1 | 5/2008 |
| WO | WO-2008050168 | A1 | 5/2008 |
| WO | WO-2008068540 | A1 | 6/2008 |
| WO | WO-2008157270 | A1 | 12/2008 |
| WO | WO-2009071464 | A1 | 6/2009 |
| WO | WO-2009071476 | A1 | 6/2009 |
| WO | WO-2009071477 | A1 | 6/2009 |
| WO | WO-2010097368 | A1 | 9/2010 |

(Continued)

OTHER PUBLICATIONS

RN 1700330-18-2, registry database compound, 2015.*
Gill et al., 2014, Curr. Pharm Des , 20(31), 5069-5076.*
Guzman et al., 2018, Journal of Neurochemistry, 146, 649-669.*
Luscher et al., 2023, Trends Pharmacol Sci, 44(9), 586-600.*
AgeneBio, Press Release, "AgeneBio Announces Additional Funding to Advance Novel GABA—A Therapeutic Program to Address Alzheimer's and Other CNS Conditions," Sep. 11, 2019; accessed at https://www.agenebio.com/agenebio-announces-additional-funding-to-advance-novel-gaba-a-therapeutic-program-to-address-alzheimers-and-other-cns-conditions.
Anagnostou, E., et al., "Autism spectrum disorder: advances in evidence-based practice," CMAJ 186:509-519, Canadian Medical Association, Canada (Apr. 2014).
Asai, Y., et al., "GABAA/Benzodiazepine receptor binding in patients with schizophrenia using [11C]Ro15-4513, a radioligand with relatively high affinity for alpha5 subunit.," Schizophrenia Res 99:333-340, Elsevier, Netherlands (Feb. 2008).

(Continued)

*Primary Examiner* — Sun Jae Yoo
(74) *Attorney, Agent, or Firm* — Sterne, Kessler, Goldstein & Fox P.L.L.C.

(57) ABSTRACT

The present invention provides compounds of formula (I) and/or salt thereof and/or biologically active metabolite thereof and/or prodrug thereof and/or solvate thereof and/or hydrate thereof and/or polymorph thereof having affinity and selectivity for the gamma-aminobutyric acid A receptor subunit alpha 5 and act as $GABA_A$ α5 negative allosteric modulators, thereby useful in the treatment or prevention of diseases related to the $GABA_A$ α5 receptor, process for the preparation and intermediates of the preparation process thereof, pharmaceutical compositions comprising them alone or in combination with one or more other active ingredients and their use as medicaments.

(I)

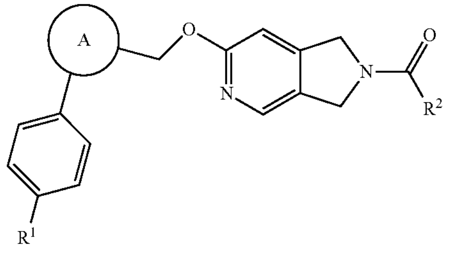

15 Claims, No Drawings

(56) References Cited

FOREIGN PATENT DOCUMENTS

| | | | |
|---|---|---|---|
| WO | WO-2010112475 | A1 | 10/2010 |
| WO | WO-2010127978 | A1 | 11/2010 |
| WO | WO-2012059482 | A1 | 5/2012 |
| WO | WO-2012062623 | A1 | 5/2012 |
| WO | WO-2012062687 | A1 | 5/2012 |
| WO | WO-2012129344 | A1 | 9/2012 |
| WO | WO-2013007387 | A1 | 1/2013 |
| WO | WO-2013057123 | A1 | 4/2013 |
| WO | WO-2014001278 | A1 | 1/2014 |
| WO | WO-2014001279 | A1 | 1/2014 |
| WO | WO-2014001281 | A1 | 1/2014 |
| WO | WO-2014001282 | A1 | 1/2014 |
| WO | WO-2014136075 | A1 | 9/2014 |
| WO | WO-2015095783 | A1 | 6/2015 |
| WO | WO-2017161370 | A1 | 9/2017 |
| WO | WO-2017133521 | A1 | 10/2017 |
| WO | WO-2018104419 | A1 | 6/2018 |
| WO | WO-2018167629 | A1 | 9/2018 |
| WO | WO-2018167630 | A1 | 9/2018 |
| WO | WO-2019104285 | A1 | 5/2019 |
| WO | WO-2019116324 | A1 | 6/2019 |
| WO | WO-2019116325 | A1 | 6/2019 |
| WO | WO-2019238633 | A1 | 12/2019 |
| WO | WO-2020012422 | A1 | 1/2020 |
| WO | WO-2020012423 | A1 | 1/2020 |
| WO | WO-2020012424 | A1 | 1/2020 |
| WO | WO-2020016443 | A1 | 1/2020 |
| WO | WO-2020065597 | A1 | 4/2020 |
| WO | WO-2020068530 | A1 | 4/2020 |
| WO | WO-2021191838 | A1 | 9/2021 |

OTHER PUBLICATIONS

Atack, J.R., et al., "In Vitro and in Vivo Properties of 3-tert-Butyl-7-(5-methylisoxazol-3-y1)-2-(1-methyl-1H-1,2,4-triazol-5-ylmethoxy)-pyrazolo[1,5-d]-[1,2,4]triazine (MRK-016), a GABAA Receptor α5 Subtype-Selective Inverse Agonist," J Pharmacol Exp Ther. 331:470-484, American Society for Pharmacology and Experimental Therapeutics, United States (Nov. 2009).

Atack, J.R., et al., "L-655,708 enhances cognition in rats but is not proconvulsant at a dose selective for alpha5-containing GABAA receptors," Neuropharmacology 51:1023-1029, Elsevier, Netherlands (Nov. 2006).

Atack, J.R., et al., "Preclinical and clinical pharmacology of the GABAA receptor alpha5 subtype-selective inverse agonist alpha5IA," Pharmacol Ther 125:11-26, Elsevier, Netherlands (Jan. 2010).

Bakker, C.E., et al., "Understanding fragile X syndrome: insights from animal models," Cytogenet Genome Res 100:111-123, Karger Publishers, Switzerland (2003).

Ballard, T.M., et al., "RO4938581, a novel cognitive enhancer acting at GABAA a5 subunit-containing receptors," Psychopharmacology 202(1-3):207-223, SAGE Publications, United States (Jan. 2009).

Bambini-Junior, V., et al., "Animal model of autism induced by prenatal exposure to valproate: behavioral changes and liver parameters," Brain Res 1408:8-16, Elsevier, Netherlands (Aug. 2011).

Batinic, B., et al., "Positive modulation of α5 GABA A receptors in preadolescence prevents reduced locomotor response to amphetamine in adult female but not male rats prenatally exposed to lipopolysaccharide," Int J Dev Neurosci 61:31-39, (Oct. 2017).

Bednar, M., et al., "Plasma and cerebrospinal fluid (CSF) pharmacokinetics of CP-457,920, a selective alpha 5 GABA-A receptor inverse agonist in young, healthy volunteers," Clin Pharmacol Ther 75:P30, American Society for Clinical Pharmacology and Therapeutics, United States (Feb. 2004).

Behlke, L.M., et al., "A Pharmacogenetic 'Restriction-of-Function' Approach Reveals Evidence for Anxiolytic-Like Actions Mediated by α5-Containing GABAA Receptors in Mice," Neuropsychopharmacology 41:2492-2501, Springer, Germany (Sep. 2016).

Biawat, P., "The Synthesis of Alpha 5 Subtype Selective GABA(A)/Benzodiazepine Receptors Ligands," 88 pages, Thesis at The University of Wisconsin-Milwaukee, United States (Aug. 2014).

Bittel, D.C., et al., "Microarray analysis of gene/transcript expression in Prader-Willi syndrome: deletion versus UPD," J Med Genet 40:568-574, BMJ, United Kingdom (Aug. 2003).

Blaszczyk, J., "Parkinson's Disease and Neuredegneration: GABA-Collapse Hypothesis," Front Neurosci, 10:269-277, Frontiers Media S.A., Switzerland (Jun. 2016).

Blatt, G.J., et al., "Density and distribution of hippocampal neurotransmitter receptors in autism: an autoradiographic study," J Autism Dev Disord 31:537-43, Springer, United States (Dec. 2001).

Bollmann, S., et al., "Developmental changes in gamma-aminobutyric acid levels in attention-deficit/hyperactivity disorder," Transl Psychiatry 8:e589, Springer, Germany (Jun. 2015).

Bolognani, F., et al., "RG1662, a Selective GABAA α5 Receptor Negative Allosteric Modulator, Increases Gamma Power in Young Adults with Down Syndrome," Abst P6.273, 67th Annual Meet Am Acad Neurol, Washington, DC, Apr. 23, 2015.

Bonin, R.P., et al., "Alpha5GABAA receptors regulate the intrinsic excitability of mouse hippocampal pyramidal neurons," J Neurophysiol 98:2244-2254, American Physiological Society, United States (Oct. 2007).

Botta, P., et al., "Regulating anxiety with extrasynaptic inhibition," Nat Neuroscience 18:1493-1500, Springer, Germany (Oct. 2018).

Braudeau, J., et al., "Specific targeting of the GABA-A receptor α5 subtype by a selective inverse agonist restores cognitive deficits in Down syndrome mice," J Psychopharmacology 25:1030-1042, SAGE Publications, United States (Aug. 2011).

Bravo-Hernandez, M., et al., "Evidence for the participation of peripheral α5 subunit-containing GABAA receptors in GABAA agonists-induced nociception in rats," Eur J Pharmacol. 734:91-97, Elsevier, Netherlands (Jul. 2014).

Caraiscos, V.B., et al., "Tonic inhibition in mouse hippocampal CA1 pyramidal neurons is mediated by alpha5 subunit-containing gamma-aminobutyric acid type A receptors," Proc Natl Acad Sci USA 2004, 101:3662-3667, National Academy of Sciences, United States (Mar. 2004).

Carrasco, M., et al., "Pharmacologic treatment of repetitive behaviors in autism spectrum disorders: evidence of publication bias," Pediatrics 129:e1301-e1310, American Academy of Pediatrics, United States (May 2012).

Carreno, F.R., et al., "Selective Pharmacological Augmentation of Hippocampal Activity Produces a Sustained Antidepressant-Like Response without Abuse-Related or Psychotomimetic Effects," Int J Neuropsychopharmacology 20:504-509, Springer, Germany (Jun. 2017).

Chambers, M.S., et al., "Identification of a novel, selective GABA(A) alpha5 receptor inverse agonist which enhances cognition," J Med Chem 46:2227-2240, American Chemical Society, United States (May 2003).

Chemical Abstracts Service, STN Database Accession No. 1936066-47-5 abstract, United States, Jun. 21, 2016.

Chemical Abstracts Service, STN Database Accession No. 2094711-87-0, United States, May 2, 2017.

Chemical Abstracts Service, STN Database Accession No. 2331259-96-0, United States, Jun. 12, 2019.

Cheng, V.Y., et al., "α5GABAA Receptors Mediate the Amnestic But Not Sedative-Hypnotic Effects of the General Anesthetic Etomidate," J Neurosci 26:3713-3720, Society for Neuroscience, United States (Apr. 2006).

Choudary, P.V., et al., "Altered cortical glutamatergic and GABAergic signal transmission with glial involvement in depression," Proc Natl Acad Sci USA 102:15653-15658, National Academy of Sciences, United States (Oct. 2005).

Christensen, J., et al., "Prenatal valproate exposure and risk of autism spectrum disorders and childhood autism," JAMA 309:1696-1703, American Medical Association, United States (Apr. 2013).

Clarkson, A.N., et al., "Reducing excessive GABA-mediated tonic inhibition promotes functional recovery after stroke," Nature 468:305-309, Springer, Germany (Nov. 2010).

(56) References Cited

OTHER PUBLICATIONS

Coghlan, S., et al., "GABA system dysfunction in autism and related disorders: from synapse to symptoms," Neurosci Biobehav Rev 36:2044-2055, Elsevier, Netherlands (Oct. 2012).
Collinson, N., et al., "An inverse agonist selective for α5 subunit-containing GABAA receptors improves encoding and recall but not consolidation in the Morris water maze," Psychopharmacology 188:619-628, SAGE Publications, United States (Nov. 2006).
Collinson, N., et al., "Enhanced Learning and Memory and Altered GABAergic Synaptic Transmission in Mice Lacking the α5 Subunit of the GABAAReceptor," J Neurosci 22:5572-5580, Society for Neuroscience, United States (Jul. 2002).
Crestani, F., et al., "Trace fear conditioning involves hippocampal alpha5 GABA(A) receptors," Proc Natl Acad Sci USA 99:8980-8985, National Academy of Sciences, United States (Jun. 2002).
Curia, G., et al., "Downregulation of tonic GABAergic inhibition in a mouse model of fragile X syndrome," Cereb Cortex 19:1515-1520, Oxford University Press, United Kingdom (Jul. 2009).
Darmani, G., et al., "Effects of the Selective α5-GABAAR Antagonist S44819 on Excitability in the Human Brain: A TMS-EMG and TMS-EEG Phase I Study," J Neurosci 36:12312-12320, Society for Neuroscience, United States (Dec. 2016).
Dawson, G.R., et al., "An inverse agonist selective for alpha5 subunit-containing GABAA receptors enhances cognition," J Pharmacol Exp Ther 316:1335-1345, American Society for Pharmacology, United States (Mar. 2006).
Du, Z., et al., "Differential Alteration in Expression of Striatal GABA A R Subunits in Mouse Models of Huntington's Disease," Front Mol Neurosci. 10:198, Frontiers Media S.A., Switzerland (Jun. 2017).
Edden, R.A., et al., "Reduced GABA Concentration in Attention-Deficit/Hyperactivity Disorder," Arch Gen Psychiatry 69:750-753, American Medical Association, United States (Jul. 2012).
Engin, E., et al., "Tonic Inhibitory Control of Dentate Gyrus Granule Cells by α5-Containing GABAA Receptors Reduces Memory Interference," J Neurosci 35:13698-13712, Society for Neuroscience, United States (Oct. 2015).
Fatemi, S.H., et al., "Glutamic acid decarboxylase 65 and 67 kDa proteins are reduced in autistic parietal and cerebellar cortices," Biol Psychiatry 52:805-810, Elsevier, Netherlands (Oct. 2002).
Fatemi, S.H., et al., "mRNA and protein levels for GABAAalpha4, alpha5, beta1 and GABABR1 receptors are altered in brains from subjects with autism," J Autism Dev Disord, 40:743-750, Springer, United States (Jun. 2010).
Fischell, J., et al., "Rapid Antidepressant Action and Restoration of Excitatory Synaptic Strength After Chronic Stress by Negative Modulators of Alpha5-Containing GABAA Receptors," Neuropsychopharmacology 40:2499-2509, Springer, Germany (Oct. 2015).
Foster, A.C., and Kemp, J.A., "Glutamate- and GABA-based CNS therapeutics," Curr Opin Pharmacol 6:7-17, Elsevier, Netherlands (Feb. 2006).
Fritschy, J.M., and Mohler, H., "GABAA-receptor heterogeneity in the adult rat brain: differential regional and cellular distribution of seven major subunits," J Comp Neural 359:154-194, Springer Science+Business Media, Germany (Aug. 1995).
Gacsalyi, I., et al., "Behavioural pharmacology of the α5-GABA A receptor antagonist S44819: Enhancement and remediation of cognitive performance in preclinical models," Neuropharmacology 125:30-38, Elsevier, Netherlands (Oct. 2017).
Gacsalyi, I., et al., Persistent therapeutic effect of a novel α5-GABA A receptor antagonist in rodent preclinical models of vascular cognitive impairment,' Eur J Pharmacol 834:118-125, Elsevier, Netherlands (Sep. 2018).
Gallos, G., et al., "Selective targeting of the α5-subunit of Gaba A receptors relaxes airway smooth muscle and inhibits cellular calcium handling," Am J Physiol Lung Cell Mol Physiol 308:L931-942, American Physiological Society, United States (May 2015).
Gill, K.M., et al., "A Novel α5GABAAR-Positive Allosteric Modulator Reverses Hyperactivation of the Dopamine System in the MAM Model of Schizophrenia," Neuropsychopharmacology 36:1903-1911, Springer, Germany (May 2011).
Glykys, J., and Mody, I., "Hippocampal network hyperactivity after selective reduction of tonic inhibition in GABA A receptor alpha5 subunit-deficient mice," Neurophysiol 95:2796-2807, American Physiological Society , United States (May 2006).
Glykys, J., et al., "Which GABAA Receptor Subunits Are Necessary for Tonic Inhibition in the Hippocampus?," J Neurosci 28:1421-1426, Society for Neuroscience, United States (Feb. 2008).
Green, M.V., and Thayer, S.A., "HIV gp120 upregulates tonic inhibition through α5-containing GABA A Rs," Neuropharmacology 149:161-168, Elsevier, Netherlands (May 2019).
Guerrini, G., and Ciciani, G., et al., "Benzodiazepine receptor ligands: a patent review," Expert Opin Ther Patents 23(7):843-866, Informa, United Kingdom (Mar. 2013).
Guidotti, A., et al., "GABAergic dysfunction in schizophrenia: new treatment strategies on the horizon," Psychopharmacology 180:191-205, SAGE Publications, United States (Jul. 2005).
Gupta, V., et al., "MEDI 17-Pyrazoloquinoline-5-Ureas as negative modulators of GABAA α5," 2 pages, 241st ACS National Meeting, Anaheim, CA, Mar. 27-31, 2011.
Han, S., et al., "Autistic-like behaviour in Scn1a+/− mice and rescue by enhanced GABA-mediated neurotransmission," Nature 489:385-390, Springer, Germany (Sep. 2012).
Hauser, J., et al., "Hippocampal α5 subunit-containing GABAA receptors modulate the expression of prepulse inhibition," Mol Psychiatry 10:201-207, Springer, Germany (Jul. 2004).
Hernandez-Reyes, J., et al., "α5GABAA receptors play a pronociceptive role and avoid the rate-dependent depression of the Hoffmann reflex in diabetic neuropathic pain and reduce primary afferent excitability," Pain 160:1448-1458, Lippincott Williams & Wilkins, United States (Jun. 2019).
Higashino, M., et al., "Lead Optimization of GABAA alpha5 Receptor Negative Allosteric Modulators," Abstract P280, XXIV International Symposium on Medicinal Chemistry, Manchester, United Kingdom Aug. 29, 2016.
Hipp, J., et al., 19th biennial IPEG Meeting, "A20 Basmisanil, a negative allosteric modulator of GABA-A alpha5 subunit-containing receptors shows target and neuronal circuit engagement in man," Neuropsychiatric Electrophysiology, 2(Suppl 1), 8, Springer Nature, Germany (2016).
Horder, J., et al., "GABA A receptor availability is not altered in adults with autism spectrum disorder or in mouse models," Sci Transl Med 10:eaam8434, American Association for the Advancement of Science, United States (Oct. 2018).
Huang, W., et al., "TBAI or KI-Promoted Oxidative Coupling of Enamines and N-Tosylhydrazine: An Unconventional Method toward 1,5- and 1,4,5-Substituted 1,2,3-Triazoles," Adv. Synth. Catal. 360:3117-3123, Wiley, United States (Aug. 2018).
International Search Report and Written Opinion for International Application No. PCT/IB2021/052486, European Patent Office, Netherlands, mailed on May 12, 2021, 14 pages.
Jacob, T.C., "Neurobiology and Therapeutic Potential of α5-GABA Type A Receptors," Front Mol Neurosci 12:Art179, Frontiers Media S.A., Switzerland (Jul. 2019).
Kammel, L.G., et al., "Enhanced GABAergic Tonic Inhibition Reduces Intrinsic Excitability of Hippocampal CA1 Pyramidal Cells in Experimental Autoimmune Encephalomyelitis," Neuroscience 395:89-100, Society for Neuroscience, United States (Dec. 2010).
Kawaharada et al., "ONO-8590580, a Novel GABAA a5 Negative Allosteric Modulator Enhances Long-Term Potentiation and Improves Cognitive Deficits in Preclinical Models," J Pharm Exp Ther 2018, 366:58-65, American Society for Pharmacology and Experimental Therapeutics, United States (Jul. 2018).
Khundakar, A.A., et al., "Analysis of primary visual cortex in dementia with Lewy bodies indicates GABAergic involvement associated with recurrent complex visual hallucinations," Acta Neuropathol Commun 2016, 4:66, Springer, Germany (Jun. 2016).
Knust, H., et al., "The discovery and unique pharmacological profile of RO4938581 and RO4882224 as potent and selective GABAA

(56) References Cited

OTHER PUBLICATIONS alpha5 inverse agonists for the treatment of cognitive dysfunction," Bioorg Med Chem Lett. 19:5940-5944, Elsevier, Netherlands (Oct. 2009).

Koh, M.T., et al., "Selective GABA(A) α5 positive allosteric modulators improve cognitive function in aged rats with memory impairment," Neuropharmacology 64:142-152, Elsevier, Netherlands (Jan. 2013).

Kwakowsky, A., et al., "GABAA receptor subunit expression changes in the human Alzheimer's disease hippocampus, subiculum, entorhinal cortex and superior temporal gyrus," J Neurochem 145:374-392, Wiley, United States (Feb. 2018).

Lake, E., et al., "The Effects of Delayed Reduction of Tonic Inhibition on Ischemic Lesion and Sensorimotor Function," J Cereb Blood Flow Metab 35:1601-1609, SAGE Publications, United States (May 2015).

Lu., C.Y., et al., "Effects of Traumatic Stress Induced in the Juvenile Period on the Expression of Gamma-Aminobutyric Acid Receptor Type A Subunits in Adult Rat Brain," Neural Plast 2017:5715816, Hindawi, United Kingdom (Mar. 2017).

Marchionni, I., et al., "In the developing rat hippocampus a tonic GABAA-mediated conductance selectively enhances the glutamatergic drive of principal cells," J Physiol. 581:515-528, Wiley, United States (May 2007).

Martin, L.J., et al., "Alpha5GABAA receptor activity sets the threshold for long-term potentiation and constrains hippocampus-dependent memory," J Neurosci 30:5269-5282, Society for Neuroscience, United States (Apr. 2010).

Martin, L.J., et al., "The physiological properties and therapeutic potential of alpha5-GABAA receptors," Biochem Soc Trans 37:1334-1337, Portland Press, United Kingdom (Dec. 2009).

Martinez-Cue, C., et al., "Reducing GABAA α5 Receptor-Mediated Inihibition Rescues Functional and Neuromorphological Defitics in a Mouse Model of Down Syndrome," J Neurosci 33: 953-966, Society for Neuroscience, United States (Feb. 2013).

Maubach, K., "GABAA Receptor Subtype Selective Cognition Enhancers," Curr Drug Targets CNS Neural Disord 2:233-239, Bentham Science Publishers, United Arab Emirates (Aug. 2003).

Mendez, M.A., et al., "The brain GABA-benzodiazepine receptor alpha-5 subtype in autism spectrum disorder: a pilot [(11)C]Ro15-4513 positron emission tomography study," Neuropharmacology 68:195-201, Elsevier, Netherlands (May 2013).

Mesbah-Oskui, L., et al., "Reduced expression of α5GABA A receptors elicits autism-like alterations in EEG patterns and sleep-wake behavior," Neurotoxicol Teratol 61:115-122, Elsevier, Netherlands (May 2017).

Mick, I., et al., "Evidence for GABA-A receptor dysregulation in gambling disorder: correlation with impulsivity," Addict Biol 22:1601-1609, Wiley, United States (Nov. 2017).

Mizuta, K., et al., "GABAA receptors are expressed and facilitate relaxation in airway smooth muscle," Am J Physiol Lung Cell Mol Physiol 294:L1206-1216, American Physiological Society, United States (Jun. 2008).

Mohamad, F.H., et al., "The α5-Containing GABAA Receptors—a Brief Summary," J Mol Neurosci 67:343-351, Springer, United States (Jan. 2019).

Mohler, H., "The legacy of the benzodiazepine receptor: from flumazenil to enhancing cognition in Down syndrome and social interaction in autism," Adv Pharmacol 72:1-36, Hindawi Publishing Corporation, United Kingdom (2015).

Mohler, H., and Rudolph, U., "Disinhibition, an emerging pharmacology of learning and memory," F1000Research, 6:101, F1000 Research Ltd., United States (Feb. 2017).

Mori, T., et al., "Evaluation of the GABAergic nervous system in autistic brain: (123)I-iomazenil SPECT study," Brain Dev 34:648-654, Elsevier, Netherlands (Sep. 2012).

Munro, G., et al., "A question of balance—positive versus negative allosteric modulation of GABA(A) receptor subtypes as a driver of analgesic efficacy in rat models of inflammatory and neuropathic pain," Neuropharmacology 61:121-132, Elsevier, Netherlands (Jul. 2011).

Murley, A.G., and Rowe, J.B., "Neurotransmitter deficits from frontotemporal lobar degeneration," Brain 5:1263-1285, Oxford University Press, United Kingdom (May 2018).

Nadler, J.J., et al., "Automated apparatus for quantitation of social approach behaviors in mice," Genes Brain Behav 3:303-314, Wiley, United States (Oct. 2004).

Neugebauer, N.M., et al., "Hippocampal GABA A antagonism reverses the novel object recognition deficit in sub-chronic phencyclidine-treated rats," Behav Brain Res 342:11-18, Elsevier, Netherlands (Apr. 2018).

Nutt, D.J., et al., "Blockade of alcohol's amnestic activity in humans by an alpha5 subtype benzodiazepine receptor inverse agonist," Neuropharmacology 53:810-820, Elsevier, Netherlands (Dec. 2007).

Oblak, A., et al., "Decreased GABAA receptors and benzodiazepine binding sites in the anterior cingulate cortex in autism," Autism Res 2:205-219, Wiley, United States (Aug. 2009).

Okamoto, K., et al., "GABAergic malfunction in the anterior cingulate cortex underlying maternal immune activation-induced social deficits," J Neuroimmunol 321:92-96, Elsevier, Netherlands (Aug. 2018).

Olsen, R.W., and Sieghart, W., "GABA A receptors: subtypes provide diversity of function and pharmacology," Neuropharmacology 56:141-148, Elsevier, Netherlands (Jan. 2009).

Olsen, R.W., and Sieghart, W., "International Union of Pharmacology. LXX. Subtypes of gamma-aminobutyric acid(A) receptors: classification on the basis of subunit composition, pharmacology, and function. Update," Pharmacol Rev 60:243-260, American Society for Pharmacology and Experimental Therapeutics, United States (Sep. 2008).

Otani, K., et al., "The GABA type A receptor alpha5 subunit gene is associated with bipolar I disorder," Neurosci Lett 381:108-113, Elsevier, Netherlands (Jun. 2005).

Poe, M.M., "Synthesis of Subtype Selective Bz/GABAA Receptor Ligands for the Treatment of Anxiety, Epilepsy and Neuropathic Pain, as Well as Schizophrenia and Asthma," Theses and Dissertations. 1301, accessed at https://dc.uwm.edu/etd/1301 (Aug. 2016).

Prevot, T.D., et al., "Insight into Novel Treatment for Cognitive Dysfunctions across Disorders," ACS Chem. Neurosci. 10:2088-2090, American Chemical Society, United States (May 2019).

Prevot, T.D., et al., "Novel Benzodiazepine-Like Ligands with Various Anxiolytic, Antidepressant, or Pro-Cognitive Profiles," Mol Neuropsychiatry 5:84-97, Karger Publishers, Switzerland (Apr. 2019).

Prut, L., et al., "A reduction in hippocampal GABAA receptor alpha5 subunits disrupts the memory for location of objects in mice," Genes Brain Behav 9:478-488, Wiley, United States (Jul. 2010).

Puts, N., et al., "Reduced GABA and altered somatosensory function in children with autism spectrum disorder," Autism Res 2016, 10:608-619, Wiley, United States (Apr. 2017).

Quirk, K., et al., "[3H]L-655,708, a novel ligand selective for the benzodiazepine site of GABAA receptors which contain the alpha 5 subunit," Neuropharmacology 35:1331-1335, Elsevier, Netherlands (Jun. 1996).

Rautio, J., et al., "Prodrugs: design and clinical applications," Nature Reviews—Drug Discovery 7:255-270, Springer, Germany (Mar. 2008).

Redrobe, J.P., et al., "Negative modulation of GABAA α5 receptors by RO4938581 attenuates discrete sub-chronic and early postnatal phencyclidine (PCP)-induced cognitive deficits in rats," Psychopharmacology 221:451-468, SAGE Publications, United States (Jun. 2012).

Ribeiro, M.J., et al., "Abnormal relationship between GABA, neurophysiology and impulsive behavior in neurofibromatosis type 1," Cortex 64:194-208, Elsevier, Netherlands (Mar. 2015).

Robertson, C.E., et al., "Reduced GABAergic Action in the Autistic Brain," Curr Biol 26:80-85, Cell Press, United States (Jan. 2016).

Roullet, F., et al., "In utero exposure to valproic acid and autism—A current review of clinical and animal studies," Neurotox Teratol. 36:47-56, Elsevier, United States (Feb. 2013).

(56) References Cited

OTHER PUBLICATIONS

Rozenweig-Lipson, S., "Structurally Diverse GABA-A α5 Positive Allosteric Modulators for Treatment of MCI due to AD,"Agenebio, Inc., accessed at https://grantome.com/grant/NIH/R44-AG063607-01, 3 pages (Aug. 2019).
Rudolph, U., and Knoflach, F., "Beyond classical benzodiazepines: novel therapeutic potential of GABAA receptor subtypes," Nat Rev Drug Discov 10:685-697, Springer, Germany (Jul. 2011).
Russo, L., et al., "A New Susceptibility Locus for Migraine with Aura in the 15q11-q13 Genomic Region Containing Three GABA-A Receptor Genes," Am J Hum Genet 76:327-333, Elsevier, Netherlands (Feb. 2005).
Savic, M.M., et al., "Are GABAA receptors containing alpha5 subunits contributing to the sedative properties of benzodiazepine site agonists?," Neuropsychopharmacology 33:332-339, Springer, Germany (Jan. 2008).
Savic, M.M., et al., "PWZ-029, a compound with moderate inverse agonist functional selectivity at GABAA receptors containing α5 subunits, improves passive, but not active, avoidance learning in rats," Brain Res 1208:150-159, Elsevier, Netherlands (May 2008).
Schipper, S., et al., "Tonic GABAA Receptors as Potential Target for the Treatment of Temporal Lobe Epilepsy," Mol Neurobiol 53:5252-5265, Springer, United States (Oct. 2015).
Sengupta, S., et al., "Could α5-GABA-A receptor activation be used as a target for managing medulloblastomas?," CNS Oncol 3:245-247, Future Medicine Ltd., United Kingdom (Jul. 2014).
Sieghart, W., and Sperk, G., "Subunit composition, distribution and function of GABA(A) receptor subtypes," Curr Top Med Chem 2:795-816, Bentham Science Publishers, United Arab Emirates (Aug. 2002).
Soh, M., and Lynch, J.W., "Selective Modulators of α5-Containing GABAA Receptors and their Therapeutic Significance," Curr Drug Targets 16:735-746, Bentham Science Publishers, United Arab Emirates (2015).
Solas, M., et al., "Treatment Options in Alzheimer's Disease: The GABA Story," Curr Pharm Des 21:4960-4971, Bentham Science Publishers, United Arab Emirates (2015).
Stamenic, T.T., et al., "Ester to amide substitution improves selectivity, efficacy and kinetic behavior of a benzodiazepine positive modulator of GABA A receptors containing the α5 subunit," Eur J Pharmacol 791:433-443, Elsevier, Netherlands (Nov. 2016).
Stephens, D.N., et al., "Role of GABAA alpha5-containing receptors in ethanol reward: the effects of targeted gene deletion, and a selective inverse agonist," Eur J Pharmacol 526:240-250, Elsevier, Netherlands (Dec. 2005).
Summary of Clinical Trial List, Search of: NCT02953639, ClinicalTrials.gov, accessed at https://clinicaltrials.gov/ct2/show/NCT02953639, accessed on Sep. 22, 2022, 9 Pages.
Summary of Clinical Trial List, Search of: NCT04299464, ClinicalTrials.gov, accessed at https://www.clinicaltrials.gov/ct2/show/NCT04299464, accessed on Sep. 22, 2022 (7 pages).
Sur, C., et al., "Autoradiographic localization of alpha5 subunit-containing GABAA receptors in rat brain," Brain Res 822:265-270, Elsevier, Netherlands (Mar. 1999).
Toso, L., et al., "Prenatal alcohol exposure alters GABA(A)alpha5 expression: a mechanism of alcohol-induced learning dysfunction," Am J Obstet Gynecol 195:522-527, Elsevier, Netherlands (Aug. 2006).
Towers, S.K., et al., "Alpha 5 subunit-containing GABAA receptors affect the dynamic range of mouse hippocampal kainate-induced gamma frequency oscillations in vitro," J Physiol 559:721-728, Wiley, United States (Sep. 2004).
Wandel, C., et al., "RG1662, a new negative allosteric modulator of the gamma-aminobutyric acid Aα5 receptor subtype, does not show convulsions at relevant doses," Eur Neuropsychopharmacol 25(Suppl2):S259, Elsevier, Netherlands (Sep. 2015).
Wang, D., et al., "Memory Deficits Induced by Inflammation Are Regulated by a5-Subunit-Containing GABAAReceptors," Cell Rep 2:488-496, Cell Press, United States (Sep. 2012).
Wang, X., et al., "Gastrodin Rescues Autistic-Like Phenotypes in Valproic Acid-Induced Animal Model," Front Neurol 9:1052, Frontiers Media S.A., Switzerland (Dec. 2018).
Wearne, T.A., et al., "GABAergic mRNA expression is differentially expressed across the prelimbic and orbitofrontal cortices of rats sensitized to methamphetamine: Relevance to psychosis," Neuropharmacology 111:107-118, Elsevier, Netherlands (Dec. 2016).
Whiting, P., et al., "GABA-A receptor subtypes in the brain: a paradigm for CNS drug discovery?," Drug Discov Today 8:445-450, Elsevier, Netherlands (May 2003).
Wisden, W., et al., "The distribution of 13 GABAA receptor subunit mRNAs in the rat brain. I. Telencephalon, diencephalon, mesencephalon," J Neurosci 12:1040-1062, Society for Neuroscience, United States (Mar. 1992).
Wu, Z., et al., "Tonic inhibition in dentate gyrus impairs long-term potentiation and memory in an Alzheimer's disease model," Nat Commun 5:4159, Springer, Germany (Jun. 2014).
Xu, N.Z., et al., "Negative allosteric modulation of alpha 5-containing GABAA receptors engenders antidepressant-like effects and selectively prevents age-associated hyperactivity in tau-depositing mice," Psychopharmacology 235:1151-1161, SAGE Publications, United States (Jan. 2018).
Yizhar, O., et al., "Neocortical excitation/inhibition balance in information processing and social dysfunction," Nature 477:171-178, Springer, Germany (Jul. 2011).
Zurek, A.A., et al., "α5GABAA receptor deficiency causes autism-like behaviors," Ann Clin Transl Neural 3:392-398, Wiley, United States (Apr. 2016).

* cited by examiner

1,3-DIHYDRO-2H-PYRROLO[3,4-C]PYRIDINE DERIVATIVES AS GABA$_A$ α5 RECEPTOR MODULATORS

CROSS-REFERENCE TO RELATED APPLICATIONS

This application is a U.S. National Phase of International Application No. PCT/IB2021/052485, filed on Mar. 25, 2021, which claims the benefit of Hungarian Patent Application No. P2000112, filed Mar. 26, 2020.

THE FIELD OF THE INVENTION

The present invention provides compounds of formula (I) having affinity and selectivity for the gamma-aminobutyric acid A receptor subunit alpha 5 (GABA$_A$ α5) and act as GABA$_A$ α5 negative allosteric modulators (GABA$_A$ α5 NAM), thereby useful in the treatment or prevention of diseases related to the GABA$_A$ α5 receptor, process for the preparation and intermediates of the preparation process thereof, pharmaceutical compositions comprising them and their use as medicaments.

THE BACKGROUND OF THE INVENTION

Gamma-aminobutyric acid (GABA) is the major inhibitory neurotransmitter in the central nervous system. Receptors sensitive for GABA are divided into two main families, the ligand gated GABA$_A$ receptors and the G-protein coupled GABA$_B$ receptors.

The ligand gated GABA$_A$ receptor mediates the majority of inhibitory neurotransmission in the mammalian brain. The receptor is composed by the pentameric assembly of multiple subunits (α1-6, β1-3, γ1-3, δ, ε, π, θ, ρ1-3) (Olsen and Sieghart, *Pharmacol Rev* 2008, 60:243-260) forming a ligand-gated $Cl^-$-channel. Subunit distribution varies developmentally and regionally in the brain. This high variability leads to broad variation in inhibitory neural mechanisms and provides the possibility for specific therapeutic interventions (Fritschy and Mohler, *J Comp Neurol* 1995, 359:154-194). Physiological roles and pharmacological profiles of GABA$_A$ receptors are strongly dependent on the subunit constitution. Studies on genetically modified mice have demonstrated that receptor subunit composition, especially regarding the α subtypes, considerably determines pharmacology of compounds acting on the benzodiazepine-sensitive allosteric modulatory site (BDZ-site) (Rudolph and Knoflach, *Nat Rev Drug Discov* 2011, 10:685-697). The widely distributed α1-containing receptors mediate the sedative and amnesic effects, whereas the α2- and α3-containing receptors account for the anxiolytic, anticonvulsant and myorelaxant effects (Sieghart and Sperk, *Curr Top Med Chem* 2002, 2:795-816; Whiting et al, Drug Discov Today 2003, 8:445-450). α5 subunit containing receptors (α5GABA$_A$Rs) are preferentially expressed in the hippocampus in both rodents and primates and thought to be implicated in cognitive functions (Wisden et al, *J Neurosci* 1992, 12:1040-1062; Quirck et al, *Neuropharmacology* 1996, 35:1331-1335; Sur et al., *Brain Res* 1999, 822:265-270).

These α5-containing receptors are predominantly extrasynaptic and mediate tonic inhibition (Caraiscos et al., *Proc Natl Acad Sci* USA 2004, 101:3662-3667). Their inhibitory effect on the excitability of hippocampal and cortical principal neurons can explain the significant effect of α5GABA$_A$Rs in cognition, learning and memory and their potential therapeutic usefulness in various disorders including, stroke, cognitive impairment, schizophrenia, depression, dementia-related conditions or diseases related to impaired social cognition or neurodevelopmental disorders such as Down syndrome or autism spectrum disorder (ASD) (Jacob, *Front Mol Neurosci* 2019, Vol 12, Art 179; Mohamad and Tarmizi Che Has, *J Mol Neurosci* 2019, 67:343-351; Soh and Lynch, *Curr Drug Targets* 2015, 16:735-746).

Early modulators acting on the BDZ-site were non-selective compounds, either GABA enhancers with anxiolytic, sedative, anaesthetic or anticonvulsant potency or partial blockers, alternatively termed as inverse agonists or negative allosteric modulators (NAMs), with cognitive enhancing effects. GABA$_A$ receptor agonists and potentiators have been characterized as effective drugs in the clinical practice (Foster and Kemp, *Curr Opin Pharmacol* 2006, 6:7-17), while NAMs have so far only been tested in animal behavior experiments and in a very few human studies (Soh and Lynch, *Curr Drug Targets* 2015; 16:735-746). The results showed beneficial activity, however, drugs non-selectively acting on many GABA$_A$ receptor subtypes resulted in undesired CNS side effects like sedation, amnesia, drug abuse, anxiety, agitation or convulsions. Thus GABA research tended to design new drugs that selectively target specific GABA$_A$ receptor subtypes among them the α5GABA$_A$Rs (Möhler, *Adv Pharmacol* 2015, 72:1-36).

Depletion of the α5 subunit revealed the role of the α5-containing receptors in neuronal plasticity (Martin et al., *J Neurosci* 2010, 30:5269-5282) and high frequency neuronal network oscillations (Glykis et al., *J Neurosci* 2008 28:1421-1426), processes fundamentally involved in attention, information processing and memory. Genetic or pharmacological reduction of the α5 subunit function resulted in significant improvement of cognitive performance in rodent models (Möhler and Rudolph, *F1000Research,* 2017 6[F1000 Faculty Rev]:101). Both in vitro and in vivo experiments showed that negative allosteric modulation of the GABA$_A$ α5 is a promising strategy in the treatment or prevention of various pathological conditions or symptoms thereof. Selective inverse agonists of α5GABA$_A$Rs, namely NGD 97-1 (Bednar et al., *Clin Pharmacol Ther* 75, 2004 75:P30), α5IA (WO 02/06285 A1; Dawson et al., *J Pharmacol Exp Ther* 2006, 316:1335-1345; Braudeau et al., *J Psychopharmacology* 2011, 25:1030-1042), L-655,708 (Quirck et al, *Neuropharmacology* 1996, 35:1331-1335; Atack et al., *Neuropharmacology* 2006, 51:1023-102), α5IA-II (WO 98/50385 A1; Collinson et al., *Psychopharmacology* 2006; 188:619-628), MRK-016 (WO 99/67245 A1; Atack et al., *J Pharmacol Exp Ther.* 2009, 331:470-484), HT-2678 (Gupta et al., 241$^{st}$ *ACS National Meeting*, Anaheim, CA, Mar. 27-31, 2011, MEDI 17), PWZ-029 (WO 2007/018660 A2; Savic et al., *Brain Res* 2008; 1208:150-159; Biawat, Thesis at The University of Wisconsin-Milwaukee, August 2014), TB-21007 (Chambers et al., *J Med Chem* 2003, 46:2227-2240), ONO-8590580 (Higashino et al., *XXIV International Symposium on Medicinal Chemistry*, Manchester, UK—Aug. 29, 2016, Abstract P280; Kawaharada et al., *J Pharm Exp Ther* 2018, 366:58-65), RO4938581 (Ballard et al., *Psychopharmacology* 2009, 202(1-3):207-223), RO4882224 (Knust et al., *Bioorg Med Chem Lett.* 2009, 19:5940-5944), basmisanil (WO 2009/071476 A1; WO 2012/059482 A1; Hipp et al., *NPFEP* 2016, 2(Suppl 1):A20) and the selective α5GABA$_A$R competitive blocker S44819 (Gacsályi et al., *Neuropharmacology* 2017, 125:30-38) as expected, proved to be effective in alleviating cognitive impairment in preclinical studies without possessing anxiogenic, proconvulsant or motor side effects. Cognitive improving effect of α5IA was demonstrated in healthy volunteers in an early pilot study (Nutt et al., *Neuropharmacology* 2007, 53:810-820). In addition, basmisanil (coded as RG1662 or RO5186582), the α5-selective compound under clinical development in schizophrenia-associated cognitive impairment (NCT02953639), resulted in significant increase in high frequency gamma oscillations in EEG activity in Down syndrome patients indicating a potential facilitatory effect on cognitive functions (Bolognani et al., 67th *Annu Meet Am Acad Neurol* Washington, DC, Apr. 23, 2015, Abst P6.273). No CNS side effects of the clinically tested α5 blockers α5IA, S44819 or basmisanil has been reported so far (Atack et al., Pharmacol Therap 2010, 125:11-26; Darmani et al., *J Neurosci* 2016, 36:12312-12320; Wandel et al., *Eur Neuropsychopharmacol* 2015 25(Suppl2):S259). On the base of preclinical data and clinical findings a favorable clinical profile of α5-subunit selective negative modulators can be predicted.

After all, due to the specific function and the compartmentalized CNS expression profile of α5GABA$_A$Rs, selective and gentle intervention, that negatively modulate its function, may have therapeutic benefit compared to non-selective agents.

Therefore, compounds having high affinity and selectivity for the α5GABA$_A$Rs, GABA$_A$ α5 NAMs respectively, can be used, alone or in combination with one or more other active ingredients, for the treatment or prevention of disorders of the central nervous system where one of the symptoms and/or syndromes of the disease may be related to the GABA$_A$ α5 receptor. These include, but not limited to neurocognitive disorders (Collinson et al., *J Neurosci* 2002, 22:5572-5580) such as Alzheimer's disease (AD) (Kwakowsky et al., *J Neurochem* 2018, 145:374-392; Solas et al., *Curr Pharm Des* 2015; 21:4960-4971; Wu et al., *Nat Commun* 2014, 4159), prodromal AD and mild cognitive impairment (Maubach, *Curr Drug Targets CNS Neurol Disord* 2003, 2:233-239), vascular cognitive impairment and vascular dementia (Gacsályi et al., *Eur J Pharmacol* 2018, 834:118-125), frontotemporal lobar degeneration including frontotemporal dementia, progressive supranuclear palsy and corticobasal syndrome (Murley and Rowe, *Brain* 2018, 5:1263-1285), Lewy body dementia (Khundakar et al., *Acta Neuropathol Commun* 2016, 4:66), age-associated memory impairment and cognitive decline (Koh et al., *Neuropharmacology* 2013, 64:142-152), cognitive impairment associated with brain cancers including but not limited to medulloblastomas (Sengupta et al., CNS Oncol 2014, 3:245-247), post-operative dementia (Cheng et al., *J Neurosci* 2006, 26:3713-3720), inflammation-induced dementia (Wang et al., Cell Rep 2012, 2: 488-496), HIV-Associated neurocognitive disorder (Green and Thayer, *Neuropharmacology* 2019, 149:161-168), cognitive impairments associated with the diseases including but not limited to migraine and tension headache (Russo et al., *Am J Hum Genet* 2005, 76:327-333), multiple sclerosis (Kammel et al., *Neuroscience* 2018, 395:89-100), Parkinson's disease (Blaszczyk, *Front Neurosci* 2016, 10:269-277), epilepsy (Schipper et al., *Mol Neurobiol* 2016, 53:5252-5265), attention deficit hyperactivity disorder and adult attention deficiency (Bollmann et al., *Transl Psychiatry* 2015, 8:e589; Edden et al., *Arch Gen Psychiatry* 2014, 69:750-753) or other CNS diseases including, but not limited to, post-traumatic stress disorder (Lu et al., *Neuronal Plast* 2017, 2017:5715816), schizophrenia (Guidotti et al., *Psychopharmacology* 2005, 180:191-205), positive, negative and/or cognitive symptoms associated with schizophrenia (Asai et al., *Schizophrenia Res* 2008, 99:333-340; Gill et al., *Neuropsychopharmacology* 2011, 36:1903-1911; Hauser et al., *Mol Psychiatry* 2005, 10:201-207; Redrobe et al., *Psychopharmacology* 2012, 221: 451-468), bipolar disorders (Otani et al., *Neurosci Lett* 2005, 381:108-113), autism spectrum disorder (ASD) (Mendez et al., *Neuropharmacology* 2013, 68:195-201), fragile X disorder (Curia et al, *Cereb Cortex* 2009, 19:1515-1520), Prader-Willi syndrome (Bittel et al., *J Med Genet* 2003, 40:568-574), Down syndrome (Braudeau et al., J *Psychopharmacology* 2011, 25:1030-1042; Martinez-Cue et al., *J Neurosci* 2013, 33: 953-966), Huntington's disease (Du et al., *Front Mol Neurosci.* 2017, 10:198), neurofibromatosis type I (Ribeiro et al., *Cortex* 2015, 64:194-208), sleep disorders (Mesbah-Oskui et al., *Neurotoxicol Teratol* 2017, 61:115-122), alcoholism (Stephens et al., *Eur J Pharmacol* 2005, 526:240-250), fetal alcohol syndrome (Toso et al., Am J Obstet Gynecol 2006, 195:522-527), mood disorders (Carreno et al., *Int J Neuropsychopharmacology* 2017, 20:504-509; Choudary et al., *Proc Natl Acad Sci USA* 2005, 102:15653-15658; Fischell et al., *Neuropsychopharmacology* 2015; 40:2499-2509), psychotic disorders (Wearne et al., *Neuropharmacology* 2016, 111:107-118), substance-induced psychotic disorder (Neugebauer et al., *Behav Brain Res* 2018, 342:11-18), anxiety disorders (Behlke et al., *Neuropsychopharmacology* 2016, 41:2492-2501; Botta et al., *Nat Neuroscience* 2015, 18:1493-1500), fear related disorders (Botta et al., *Nat Neuroscience* 2015, 18:1493-1500; Crestani et al., *Proc Natl Acad Sci USA* 2002, 99:8980-8985), stress disorder (Fischell et al., *Neuropsychopharmacology* 2015; 40:2499-2509), behavioural or drug addictions (Mick et al., *Addict Biol* 2017, 22:1601-1609), Alzheimer's disease related neuropsychiatric symptoms (Xu et al., *Psychopharmacology* 2018, 235:1151-1161), stroke (Clarkson et al., *Nature* 2010, 468:305-309; Lake et al., *J Cereb Blood Flow Metab* 2015, 35:1601-1609), neuropathic pain (Hérnandez-Reyes et al., *Pain* 2019, 160:1448-1458) and inflammatory pain (Bravo-Hernández et al., *Eur J Pharmacol.* 2014, 734:91-97; Munro et al., *Neuropharmacology* 2011, 61:121-132). Modulating α5GABA$_A$Rs may also be beneficial in treating diseases and conditions including, but not limited to bronchoconstrictive diseases such as but not limited to asthma, chronic obstructive pulmonary disease, and bronchopulmonary dysplasia (Gallos et al., *Am J Physiol Lung Cell Mol Physiol* 2015, 308:L931-942; Mizuta et al., *Am J Physiol Lung Cell Mol Physiol* 2008, 294:L1206-1216). Compounds capable of modulating α5GABA$_A$Rs are in particular expected to be useful candidates for the treatment of neurocognitive disorders, Alzheimer's disease, and schizophrenia.

Numerous structurally different compounds active on the α5 subunit of the GABA$_A$ receptor are known in the art (Guerrini et al., *Expert Opin Ther Patents* 2013, 23(7):843-866), including isoxazole (e.g. WO 2009/071464 A1, WO 2009/071477 A1, WO 2010/097368 A1, WO 2010/112475 A1, WO 2010/127978 A1) and triazole derivatives (e.g. WO 2012/062687 A1, WO 2014/001281 A1).

Certain isoxazole and triazole derivatives as agonists of the NR1 H4 (farnesoid X or FXR) receptor are described in e.g. WO 2017/133521 A1, WO 2013/007387 A1, WO 2008/157270 A1 or WO 2007/140174 A2.

Despite the numerous studies and modulators of the GABA$_A$ α5 receptor, unmet need still persists to provide compounds that can be useful in the treatment or prevention of diseases related to the GABA$_A$ α5 receptor.

SUMMARY OF THE INVENTION

The present invention provides compounds of formula (I)

(I)

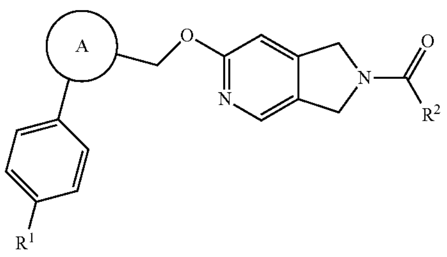

wherein
A is represented by

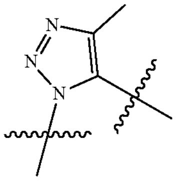
group,
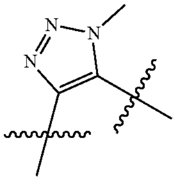
group, or
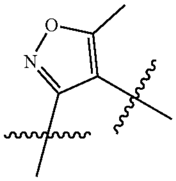
group, $R^1$ is hydrogen or halogen,
$R^2$ is $C_{1-4}$alkyl group,
and/or salts thereof and/or biologically active metabolites thereof and/or prodrugs thereof and/or solvates thereof and/or hydrates thereof and/or polymorphs thereof.

The present invention provides a compound of formula (I), as defined above for use in the treatment or prevention of diseases related to the $GABA_A$ α5 receptor.

The present invention provides the use of a compound of formula (I), as defined above, for the manufacture of a medicament for the treatment or prevention of diseases related to the $GABA_A$ α5 receptor.

The present invention provides a method of treating or preventing diseases related to the $GABA_A$ α5 receptor comprising administering to a subject, including humans, in need of such treatment or prevention an effective amount of at least one compound of formula (I), as defined above.

The present invention provides the combinational use of compounds of formula (I) as defined above, with one or more other active ingredients for the treatment or prevention of diseases related to the $GABA_A$ α5 receptor.

The present invention provides pharmaceutical compositions containing the compound of formula (I), as defined above as active ingredients.

The present invention provides medicaments (combinational pharmaceutical compositions) comprising a combination of the compound of formula (I), as defined above with one or more other active ingredients.

The present invention provides pharmaceutical compositions containing the compound of formula (I), as defined above as active ingredients alone or in combination with one ore more other active ingredients for use in the treatment or prevention of diseases related to the $GABA_A$ α5 receptor.

The present invention provides a process for the manufacture of the compounds of formula (I), as defined above and intermediates of the preparation process as well.

The present invention also provides a chemical or pharmaceutical preparation of pharmaceutical compositions containing the compounds of formula (I), as defined above alone, or in combination with one ore more other active ingredients.

DETAILED DESCRIPTION OF THE INVENTION

The present invention provides compounds of formula (I) having affinity and selectivity for the alpha 5 subunit-containing gamma-aminobutyric acid A receptor ($GABA_A$ α5 receptor) and act as $GABA_A$ α5 receptor negative allosteric modulators, thereby useful in the treatment or prevention of diseases related to the $GABA_A$ α5 receptor, process for the preparation thereof, pharmaceutical compositions comprising them alone or in combination with one or more other active ingredients and their use as medicaments.

The present invention relates to compounds of formula (I)

(I)

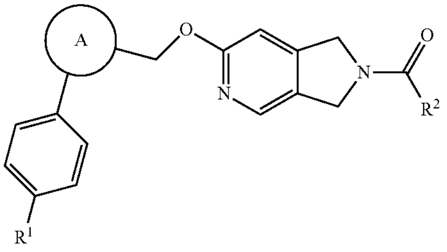

wherein
A is represented by

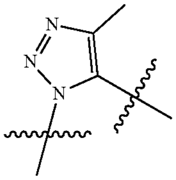
group,
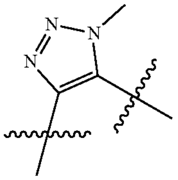
group, or
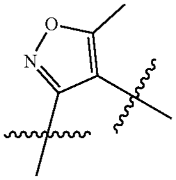
group, $R^1$ is hydrogen or halogen,
$R^2$ is $C_{1-4}$alkyl group,
and/or salts thereof and/or biologically active metabolites thereof and/or prodrugs thereof and/or solvates thereof and/or hydrates thereof and/or polymorphs thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The nomenclature used is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

Definition of the general terms used herein, whether or not the terms in question are presented individually or in combination with other groups are described below.

"Optional" or "optionally" means that the subsequently described event or circumstance may but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents.

Where any group may carry multiple substituents and a variety of possible substituents is provided, the substituents are independently selected and need not to be the same.

The term "unsubstituted" means that the specified group bears no substituents.

The term "$C_{1-4}$alkyl" refers alone or in combination with other groups to a straight or branched, single or multiple branched, hydrocarbon radical and consists of 1 to 4 carbon atoms. Examples include, but are not limited to, methyl, ethyl, propyl, i-propyl (isopropyl), n-butyl, 2-butyl (sec-butyl) or t-butyl (tert-butyl) group.

The term "halogen", "halo" or "halide" refers alone or in combination with other groups to fluoro (fluorine), chloro (chlorine), bromo (bromine) or iodo (iodine), preferably fluoro (fluorine), chloro (chlorine) or bromo (bromine).

The terms "compound(s) of this invention", "compound(s) of the present invention" "compounds of formula (I), as defined above" refers to compounds of formula (I) and/or salts thereof and/or biologically active metabolites thereof and/or prodrugs thereof and/or solvates thereof and/or hydrates thereof and/or polymorphs thereof.

The term "salt" refers to pharmaceutically acceptable and/or to pharmaceutically non-acceptable salts.

The term "pharmaceutically acceptable salt" refers to a conventional acid addition or base addition salt which preserves the biological efficacy and properties of the compounds of formula (I) and which can be formed with suitable non-toxic organic or inorganic acids or organic or inorganic bases. Examples of acid addition salts include salts derived from inorganic acids, such as, but not limited to, hydrochloric acid, hydrobromic acid, hydroiodic acid, sulfuric acid, sulphamic acid, phosphoric acid, nitric acid and perchloric acid and derived from various organic acids, such as, but not limited to, acetic acid, propionic acid, benzoic acid, glycolic acid, phenylacetic acid, salicylic acid, malonic acid, maleic acid, oleic acid, pamoic acid, palmitic acid, benzenesulfonic acid, toluenesulfonic acid, methanesulfonic acid, oxalic acid, tartaric acid, succinic acid, citric acid, malic acid, lactic acid, glutamic acid, fumaric acid and the like. Examples of base addition salts are salts derived from ammonium-, potassium-, sodium- and quaternary ammonium hydroxides such as tetramethylammonium hydroxide. These salts often exhibit more favorable solubility properties than the compounds used for their preparation and are therefore more suitable for use in the preparation of various pharmaceutical formulations.

The "pharmaceutically non-acceptable salts" may be preferred for the purification or isolation of the compounds of formula (I) and are therefore also within the scope of the invention.

The term "prodrug" refers to derivatives of compounds of formula (I) according to the invention which themselves have no therapeutic effect but containing such groups which, after in vivo chemical or metabolic degradation (biotransformation) become "biologically active metabolite" which is responsible for the therapeutic effect. Such decomposing groups associated with the compounds of formula (I) of the present invention, in particular those suitable for prodrugs, are known in the art and may also be applied for the compounds of the present invention (Rautio et al., *Nature Reviews—Drug Discovery* 2008, 7:255-270).

The compounds of formula (I) may exist in various polymorphic forms. As is known in the art, polymorphism is the ability of a compound to crystallize in more than one crystalline form, i.e. in polymorphic form. Polymorphic forms of a particular compound can be defined by identical chemical formula or composition and differ in their chemical structure as crystalline structures of two different chemical compounds.

The compounds of formula (I) and salts thereof may also be present as solvates or hydrates, which are also within the scope of the invention. The term "solvate" refers to non-covalent stoichiometric or nonstoichiometric combinations of solvent and solute. The term "hydrate" refers to non-covalent stoichiometric or nonstoichiometric combinations of water and solute.

The present invention provides pharmaceutical compositions comprising at least one compound of formula (I), as defined above as active ingredient.

The present invention provides pharmaceutical compositions comprising a combination of the compound of formula (I), as defined above with one or more other active ingredients. The pharmaceutical composition may comprise at least one compound of the invention together with one ore more other active ingredients in a single dosage form or separately. The combinational composition may be administered simultaneously, separately or sequentially.

The term "pharmaceutical composition" (or "composition") refers to a mixture or solution comprising a therapeutically effective amount of an active ingredient together with pharmaceutically acceptable excipients to be administered to a subject, e.g., a human in need thereof.

The present invention also relates to the chemical and pharmaceutical preparation of pharmaceutical compositions.

The pharmaceutical compositions of the present invention may be formulated in various pharmaceutical formulations, such as, but not limited to, solid oral dosage forms such as tablets (e.g., buccal, sublingual, effervescent, chewable, orally dispersible), capsules, pills, pilulas, orally dispersible films, granules, powders; liquid formulations such as solutions, emulsions, suspensions, syrups, elixirs, drops; parenteral dosage forms such as intravenous injections, intramuscular injections, subcutaneous injections; other forms of medicine such as eye drops, semi-solid ophthalmic preparations, semi-solid dermal preparations (such as ointments, creams, pastes), transdermal therapeutic systems, suppositories, rectal capsules, rectal solutions, emulsions and suspensions, etc.

The pharmaceutical compositions of the present invention may be administered in various ways, such as, but not limited to oral, rectal, mucous, transdermal or intestinal administration; parenteral administration including intramuscular, subcutaneous, intravenous, intramedullary injections as well as intraarticular, intrathecal, direct intraventricular, intraperitoneal, intranasal or intraocular injections and eye drops.

Alternatively, the compounds may be administered locally and not systemically, for example by direct injection of the compound to the kidney or the heart, often in a modified release formulation. In addition, the drug may be administered in a targeted carrier system, for example in a tissue-specific antibody encapsulated liposome. The liposomes transfer the active agent selectively to the target organ, which absorbs it.

The pharmaceutical composition may be administered in various ways and in various pharmaceutical forms. The compound of the invention may be administered alone or in combination with pharmaceutically acceptable excipients, in single or multiple doses. The dose required to achieve the appropriate therapeutic effect may vary widely and must always be adapted to individual needs with regard to the degree of disease, the condition and weight of the patient being treated and the sensitivity to the active ingredient, the way of dosage regimen and the numbers of daily treatments.

For simple administration, it is preferred that the pharmaceutical compositions consist of dosage units that contain the amount of active ingredient(s) to be administered once, or a small number of multiple, or half, one third, a quarter. Such dosage units are, for example, tablets that can be provided with a half or quarter groove to facilitate half or quarter-splitting of the tablet in order to weigh the required amount of active ingredient(s).

Pharmaceutical compositions containing the active ingredient(s) according to the invention generally contain from 0.01 to 500 mg of active ingredient(s) per dosage unit. It is of course also possible that the amount of active ingredient(s) in each formulation exceeds the above limit either up or down.

The present invention relates also to pharmaceutical compositions for use in pediatric use such as, but not limited to, solutions, syrups, elixirs, suspensions, powders for the preparation of suspensions, dispersible or effervescent tablets, chewable tablets, orodispersible tablets, tablets or coated tablets, orally sparkling powders or granules, capsules.

The pharmaceutical compositions of the present invention may be prepared by methods known per se such as conventional mixing, dissolution, emulsification, suspending, microencapsulation, freeze drying, extrusion and spheronization, lamination, film coating, granulation, encapsulation, drageage or pressing.

The pharmaceutical compositions of the present invention may be formulated in the usual way using one or more physiologically (or pharmaceutically) acceptable excipients which promote the incorporation of the active ingredient into pharmaceutically acceptable pharmaceutical forms. The term "physiologically or pharmaceutically acceptable excipient" denotes any ingredient used in formulating pharmaceutical products which have no therapeutic activity and non-toxic. The proper formulation depends on the mode of administration chosen. Any of the techniques and excipients well known in the art can be used.

The excipients applicable in the preparation may be selected from the following categories, such as, but not limited to, fillers of tablets and capsules, binders of tablets and capsules, modified drug release agents, disintegrants, glidants, lubricants, sweeteners, taste-masking agents, flavorants, coating materials, surfactants, stabilizers, preservatives or antioxidants, buffering agents, complexing agents, wetting or emulsifying agents, salts for adjusting the osmotic pressure, lyophilization excipients, microencapsulating agents, ointment materials, penetration enhancers, solubilizers, solvents, suppository materials, suspending agents. Suitable pharmaceutical excipients can be for example: starch, microcrystalline cellulose, talc, glucose, lactose, gelatin, silica, talc, magnesium stearate, sodium stearate, glycerol monostearate, cellulose derivatives, sodium chloride, glycerol, propylene glycol, water, ethanol and the like.

Another embodiment of the present invention relates to the use of special binders that can improve the solubility, dissolution, penetration, absorption or bioavailability of the active ingredient(s), such as, but not limited to, hydrophilic polymers, hot melting extruding excipients, surfactants, buffering agents, complexing agents, emulsifying agents, lyophilization excipients, disintegrants, microencapsulating agents, penetration promoters, solubilizers, cosolvents, suspending agents.

The excipients described above and the various methods of preparation are only representative examples. Other materials and process techniques known in the art may also be used.

The term "other active ingredient" refers to therapeutic agents including, but not limited to acetylcholinesterase inhibitors (such as galantamine, rivastigmine, donepezil, tacrine, phenserine, ladostigil and ABT-089); NMDA receptor agonists or antagonists (such as memantine, neramexane, EVT101, and AZD4282); anti-amyloid antibodies including anti-amyloid humanized monoclonal antibodies (such as bapineuzumab, ACCOOl, CAD 106, AZD3102, H12A11V1); beta-(such as verubecestat, and AZD3293) or gamma-secretase inhibitors (such as LY450139 and TAK 070) or modulators; tau phosphorylation inhibitors; ApoE4 conformation modulators; p25/CDK5 inhibitors; NK1/NK3 receptor antagonists; COX-2 inhibitors (such as celecoxib, rofecoxib, valdecoxib, 406381 and 644784); LRRK2 inhibitors; HMG-CoA reductase inhibitors; NSAIDs (such as ibuprofen); vitamin E; glycine transport inhibitors; glycine site antagonists (such as lacosamide); LXR β agonists; androgen receptor modulators; blockers of Aβ oligomer formation; NR2B antagonists, anti-inflammatory compounds (such as (R)-flurbiprofen, nitroflurbiprofen, ND-1251, VP-025, HT-0712, and EHT-202); PPAR gamma agonists (such as pioglitazone and rosiglitazone); CB-1 receptor antagonists or inverse agonists (such as AVE1625); CB-2 agonists (such as 842166 and SAB378); VR-1 antagonists (such as AMG517, 705498, 782443, PAC20030, VI 14380 and A425619); bradykinin BI receptor antagonists (such as SSR240612 and NVPSAA164); sodium channel blockers and antagonists (such as VX409 and SPI860); NOS inhibitors (such as SD6010 and 274150); antibiotics; growth hormone secretagogues (such as ibutamoren, ibutamoren mesylate, and capromorelin); potassium channel openers; AMPA agonists or AMPA modulators (such as CX-717, LY 451395, LY404187 and S-18986); GSK3 inhibitors (such as AZD1080, SAR502250 and CEP16805); neuronal α7 nAChR agonists or PAMs (such as ABT-126, AZD0328, EVP-6124, AVL-3288 or PNU-120596); MARK ligands; M1 or M4 mAChR agonists or PAMs; mGluR2 antagonists or NAMs or PAMs; mGluR5 antagonists (such as AZD9272); alpha agonists; ADAM-10 ligands; sedatives, hypnotics, anxiolytics, antipsychotics, cyclopyrrolones, imidazopyridines, pyrazolopyrimidines, minor tranquilizers, melatonin agonists and antagonists, melatonergic agents; orexin antagonists and agonists; prokineticin agonists and antagonists; T-type calcium channel antagonists; triazolopyridines benzodiazepines, barbiturates; 5-HT1A antagonists (such as lecozotan); 5-HT2 antagonists; 5-HT4 agonists (such as PRX-03140); 5-HT6 antagonists (such as GSK 742467, SGS-518, FK-962, SL-65.0155, SRA-333 and xaliproden); histamine H3 receptor antagonists and inverse agonists (such as S38093, ABT-834, ABT 829, GSK 189254 and CEP16795); PDE4 inhibitors (such as HT0712); PDE9 inhibitors (such as BI40936); PDE10 inhibitors; HDAC inhibitors; KCNQ antagonists; $GABA_A$ signaling enhancers (such as AZD-7325, PF-06372865, L-838,417, TPA-023, brexanolone, zuranolone, alphaxalone, ganaxolone, gaboxadol, tiagabine, vigabatrine, bumetanide), and blockers (such as S44819), $GABA_B$ signalling enhancers (such as baclofen), V1a receptor antagonists (such as balovaptan); MAO-B inhibitors; dopamine transport inhibitors; noradrenaline transport inhibitors; D2 agonists and partial agonists; anticholinergics (such as biperiden); COMT inhibitors (such as entacapone); A2a adenosine receptor antagonists; cholinergic agonists; compounds from the phenothiazine, thioxanthene (such as chlorprothixene and thiothixene), heterocyclic dibenzazepine (such as clozapine), butyrophenone (such as haloperidol), diphenylbutylpiperidine (such as pimozide) and indolone (such as molindolone) classes of neuroleptic agents; loxapine, sulpiride; atypical antipsychotics (such as aripiprazole, asenapine, brexpiprazole, cariprazine, iloperidone, lurasidone, olanzapine, paliperidone, quetiapine, risperidone and ziprasidone); levodopa; calcium channel blockers (such as ziconotide and NMED160); MMP inhibitors; thrombolytic agents; opioid analgesics (such as codeine, fentanyl, hydromorphone, levorphanol, meperidine, methadone, morphine, oxycodone, oxymorphone, pentazocine, propoxyphene); pranipexole; ropinirole; neutrophil inhibitory factor; SSRIs or SSNRIs; tricyclic antidepressant drugs; norepinephrine modulators; lithium; valproate; gabapentin; pregabalin; rizatriptan; zolmitriptan; naratriptan and sumatriptan or other drugs that affect receptors or enzymes that either increase the efficacy, safety, convenience, or reduce unwanted side effects or toxicity of the compounds of the present invention.

In one embodiment, the other active ingredient refers to an acetylcholinesterase inhibitor (such as galantamine, rivastigmine, donepezil, tacrine, phenserine, ladostigil and ABT-089); NMDA receptor agonist or antagonist (such as memantine, neramexane, EVT101, and AZD4282); anti-amyloid antibody including anti-amyloid humanized monoclonal antibody (such as bapineuzumab, ACCOOl, CAD 106, AZD3102, H12A11V1); beta-(such as verubecestat, and AZD3293) or gamma-secretase inhibitor (such as LY450139 and TAK 070) or modulator; tau phosphorylation inhibitor; ApoE4 conformation modulator; glycine transport inhibitor; AMPA agonist or AMPA modulator (such as CX-717, LY 451395, LY404187 and S-18986); neuronal α7 nAChR agonist or PAM (such as ABT-126, AZD0328, EVP-6124, AVL-3288 or PNU-120596); 5-HT6 antagonist (such as GSK 742467, SGS-518, FK-962, SL-65.0155, SRA-333 and xaliproden); histamine H3 receptor antagonist and inverse agonist (such as S38093, ABT-834, ABT 829, GSK 189254 and CEP16795); $GABA_A$ signaling enhancer (such as AZD-7325, PF-06372865, L-838,417, TPA-023, brexanolone, zuranolone, alphaxalone, ganaxolone, gaboxadol, tiagabine, vigabatrine, bumetanide), and blocker (such as S44819), $GABA_B$ signalling enhancer (such as baclofen), V1a receptor antagonist (such as balovaptan); D2 partial agonist; cholinergic agonist; a compound from the phenothiazine, thioxanthene (such as chlorprothixene and thiothixene), heterocyclic dibenzazepine (such as clozapine), butyrophenone (such as haloperidol), diphenylbutylpiperidine (such as pimozide) and indolone (such as molindolone) classes of neuroleptic agents; loxapine, sulpiride; or an atypical antipsychotic (such as aripiprazole, asenapine, brexpiprazole, cariprazine, iloperidone, lurasidone, olanzapine, paliperidone, quetiapine, risperidone and ziprasidone).

The term "modulators" refers to molecules interacting with the target receptor, wherein the interaction can be e.g. agonistic, antagonistic or inverse agonistic.

The term "inhibitors" referes to molecules competing with, reducing or preventing the binding of a particular ligand to a particular receptor or reducing or preventing the inhibition of the function of a particular protein.

The term "agonists" refers to compounds having affinity to a receptor binding site and enhancing the activity of the receptor-mediated response. "Full-agonists" effect a full response, "partial agonists" effects less than full activation even when occupying the total receptor population.

The term "inverse agonists" refers to compounds producing an effect opposite to that of an agonist by binding to the same agonist binding site, or reducing the effect of an agonist by binding at a different allosteric binding site.

The term "antagonists" refers to compounds diminishing or preventing the action of another compound or receptor site, or attenuating the effect of an agonist. "Competitive antagonists" bind to the same site as the agonist but does not activate it, thus blocks the agonists' action. "Non-competitive antagonists" binds to an allosteric site on the receptor to prevent activation of the receptor. Binding of "reversible antagonists" to a receptor is non-covalent (can be washed out), while binding of "irreversible antagonists" is covalent (cannot be washed out).

The term "allosteric modulators" refers to compounds binding to a receptor at a site distinct from the agonist binding site, i.e. to the allosteric site, wherein by inducing conformational change in the receptor, alter the affinity and/or activity of the receptor for the endogenous ligand or agonist. "Positive allosteric modulators" or "PAMs" increase the affinity, whilst "negative allosteric modulators" or "NAMs" decrease the affinity thereby decrease the activity of a receptor indirectly. The compounds of formula (I), as defined above are negative allosteric modulators binding to the benzodiazepine binding site with inverse agonism selective for the $GABA_A$ α5 receptor.

The term "inhibition constant" ($K_i$) refers to the absolute binding affinity of a particular inhibitor to a receptor. It is measured using competition binding assays and is equal to the concentration where the particular inhibitor would occupy half of the receptors if no competing ligand was present. $K_i$ values can be converted logarithmically to $pK_i$ values ($-\log K_i$) in which higher values indicate exponentially greater potency.

The term "submaximal effective concentration" refers to the concentration of a particular compound required for obtaining 10% of the maximum of a particular effect.

The term "functional selectivity" refers to the different degrees of modulation by a particular compound at different receptor subtypes. In the present invention, a compound is particularly functional selective if it acts as inverse agonist at $GABA_A$ α5 receptor by reducing the effect of GABA by more than 30%, while affecting the other $GABA_A$ receptor subtypes by less than 15%.

The terms "condition", "defect", "deficit", "disability", "disorder", "disease" or "disease state" are used interchangeably to denote any disease, condition, symptom, syndrome, disorder or indication.

The term "diseases related to the $GABA_A$ α5 receptor" refers to diseases, conditions or disorders of the central nervous system where one of the symptoms and/or syndromes of the disease may be related to the $GABA_A$ α5 receptor. These diseases include, but not limited to, neurodegenerative disorders, neurocognitive disorders, neurodevelopmental disorders, schizophrenia, mood disorders, pain disorders, substance-related and addictive disorders or other diseases.

The term "cognition" refers to the processes a subject, preferably a mammal, more preferably a human, uses to organize information, including acquiring information (perception), selecting (attention), representing (understanding) and retaining (memory) information, and using it to guide behavior (reasoning and coordination of motor outputs). Interventions to improve cognitive function may be directed at any one of these core faculties.

In one embodiment, the compounds of formula (I), as defined above are useful as cognition enhancers. The term "cognition enhancer" refers to the improvement of cognitive functions, particularly social cognition, complex attention, executive function, perceptual-motor function, language or learning and memory. Cognitive enhancement is an intervention that improves a subsystem in some way other than repairing something that is broken or remedying a specific dysfunction.

The diseases related to the $GABA_A$ α5 receptor may show comorbidity with each other. Comorbidity indicates a medical condition existing simultaneously but independently with another condition in a patient, or a medical condition in a patient that causes, is caused by, or is otherwise related to another condition in the same patient. However, in psychiatric, psychologic, or mental health diseases comorbidity does not necessarily imply the presence of multiple diseases, but instead can reflect our current inability to supply a single diagnosis that accounts for all symptoms.

The term "neurodegenerative disorder" includes, but not limited to, Alzheimer's disease (AD), Huntington's disease (HD), Parkinson's disease (PD), or amyotrophic lateral sclerosis (ALS).

The term "neurocognitive disorder" includes, but not limited to, cognition deficiency disorders, memory deficits, age-associated memory impairment or cognitive decline, dementia (or different forms thereof such as dementia in Alzheimer's disease, Niemann Pick-disease, Parkinson's disease, or Huntington's disease, dementia with Lewy bodies (DLB), frontotemporal dementia, vascular dementia (VaD), subcortical dementia, mixed vascular and subcortical dementia, multi-infarct dementia, post-operative dementia, or inflammation-induced dementia), Alzheimer's disease related neuropsychiatric symptoms, mild cognitive impairment (MCI), vascular cognitive impairment (VCI), CNS conditions occurring after stroke, cognitive impairment associated with brain cancers (including but not limited to medulloblastomas), cognitive decline in Down Syndrome (DS), cognitive dysfunction in major depressive disorder (MDD) or HIV-Associated neurocognitive disorder.

The term "neurodevelopmental disorder" includes, but not limited to, Down syndrome or autism spectrum disorder (ASD).

The term "schizophrenia" includes, but not limited to, different forms of schizophrenia, positive, negative and/or cognitive symptoms associated with schizophrenia, schizotypal and delusional disorders.

The term "pain disorder" includes, but not limited to, nociceptive, neuropathic or inflammatory pain.

The term "mood disorder" includes, but not limited to, depression-related disorders (such as major depressive disorder (MDD), dysthymia, cyclothymic disorder, seasonal affective disorder/seasonal depression, depression after traumatic brain injury (TBI), postpartum depression, premenstrual dysphoric disorder, depressive symptoms associated with menopause, depression following substance abuse/withdrawal, bipolar disorders, bipolar disorder in remission, or depressive episodes of bipolar disorder), bipolar disorders, substance (alcohol or drug) induced, or not otherwise specified mood disorders (MD-NOS).

The term "other disease" includes, but not limited to, attention deficit hyperactivity disorder and adult attention deficiency, other stress related conditions, stroke, neurofibromatosis type I, multiple sclerosis, acute meningitis, alcoholism, fetal alcohol syndrome, or bronchoconstrictive diseases (such as asthma, chronic obstructive pulmonary disease, and bronchopulmonary dysplasia).

In one embodiment, the disease related to the $GABA_A$ α5 receptor refers to Alzheimer's disease (AD), Huntington's disease (HD), Parkinson's disease, amyotrophic lateral sclerosis (ALS), cognition deficiency disorders, memory deficits, age-associated memory impairment or cognitive decline, dementia or different forms thereof such as dementia in Alzheimer's disease, Niemann Pick-disease, Parkinson's disease, or Huntington's disease, dementia with Lewy bodies (DLB), frontotemporal dementia, vascular dementia (VaD), subcortical dementia, mixed vascular and subcortical dementia, multi-infarct dementia, post-operative dementia, or inflammation-induced dementia), Alzheimer's disease related neuropsychiatric symptoms, mild cognitive impairment (MCI), vascular cognitive impairment (VCI), CNS conditions occurring after stroke, cognitive impairment associated with brain cancers (including but not limited to medulloblastomas), cognitive decline in Down Syndrome (DS), cognitive dysfunction in major depressive disorder (MDD), HIV-Associated neurocognitive disorder; Down Syndrome (DS), autism spectrum disorder (ASD); different forms of schizophrenia, positive, negative and/or cognitive symptoms associated with schizophrenia, schizotypal and delusional disorders; nociceptive, neuropathic or inflammatory pain; depression-related disorders (such as major depressive disorder (MDD), dysthymia, cyclothymic disorder, seasonal affective disorder/seasonal depression, depression after traumatic brain injury (TBI), postpartum depression, premenstrual dysphoric disorder, depressive symptoms associated with menopause, depression following substance abuse/withdrawal, bipolar disorders, bipolar disorder in remission, or depressive episodes of bipolar disorder), bipolar disorders, substance (alcohol or drug) induced, not otherwise specified mood disorders (MD-NOS); attention deficit hyperactivity disorder and adult attention deficiency, other stress related conditions, stroke, neurofibromatosis type I, multiple sclerosis, acute meningitis, alcoholism, fetal alcohol syndrome, or bronchoconstrictive diseases (such as asthma, chronic obstructive pulmonary disease, and bronchopulmonary dysplasia).

In one embodiment, the disease related to the $GABA_A$ α5 receptor refers to Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia.

The present invention provides a method of treating or preventing diseases related to the $GABA_A$ α5 receptor, or for cognition enhancement, comprising administering to a subject, preferably a mammal, more preferably a human being, in need of such treatment or prevention, therapeutically effective amount of a compound of formula (I), as defined above alone or with at least one pharmaceutically acceptable excipient in the form of a pharmaceutical formulation.

The present invention provides a method of treating or preventing diseases related to the $GABA_A$ α5 receptor, or for cognition enhancement, comprising administering to a subject, preferably a mammal, more preferably a human being, in need of such treatment or prevention, therapeutically effective amount of a compound of formula (I), as defined above in combination with one or more other active ingredients.

The present invention provides a method of treating or preventing of neurodegenerative disorders, neurocognitive disorders, neurodevelopmental disorders, schizophrenia, mood disorders, pain disorders, substance-related and addictive disorders or other diseases, or at least one of the symptoms and/or syndromes thereof, where one of the symptoms and/or syndromes of the disease may be related to the $GABA_A$ α5 receptor, in a subject, preferably a mammal, more preferably a human being, suffering therefrom, or for cognition enhancement. This method of treatment comprises administering to a subject, preferably a mammal, more preferably a human being, in need of such treatment or prevention, therapeutically effective amount of the compound of formula (I), as defined above. The method of treatment may include administering to a subject preferably a mammal, more preferably a human being, in need of such treatment therapeutically effective amount of a pharmaceutical composition comprising the compound of formula (I), as defined above.

The present invention provides a method of treating or preventing Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia, or at least one of the symptoms and/or syndromes thereof, in a subject, preferably a mammal, more preferably a human being, suffering therefrom, or for cognition enhancement comprising administering a therapeutically effective amount of the compound of formula (I), as defined above.

The present invention provides the compound of formula (I), as defined above for use in the treatment or prevention of diseases related to the $GABA_A$ α5 receptor, or for use as cognition enhancer.

The present invention provides the compound of formula (I), as defined above in combination with one or more other active ingredients for use in the treatment or prevention of diseases related to the $GABA_A$ α5 receptor, or for use as cognition enhancer.

The present invention provides the compound of formula (I), as defined above for use in the treatment or prevention of neurodegenerative disorders, neurocognitive disorders, neurodevelopmental disorders, schizophrenia, mood disorders, pain disorders, substance-related and addictive disorders or other diseases, or at least one of the symptoms and/or syndromes thereof, or as cognition enhancer.

The present invention provides the compound of formula (I), as defined above for use in the treatment or prevention of Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia, or at least one of the symptoms and/or syndromes thereof, or as cognition enhancer.

The present invention provides the use of the compound of formula (I), as defined above for the manufacture of a medicament for the treatment or prevention of diseases related to the $GABA_A$ α5 receptor, or for cognition enhancement.

The present invention provides the use of the compound of formula (I), as defined above in combination with one or more other active ingredients, for the manufacture of a medicament for the treatment or prevention of diseases related to the $GABA_A$ α5 receptor, or for cognition enhancement.

The present invention provides the use of the compound of formula (I), as defined above for the manufacture of a medicament for the treatment or prevention of neurodegenerative disorders, neurocognitive disorders, neurodevelopmental disorders, schizophrenia, mood disorders, pain disorders, substance-related and addictive disorders or other diseases, or at least one of the symptoms and/or syndromes thereof, or for cognition enhancement.

The present invention provides the use of the compound of formula (I), as defined above for the manufacture of a medicament for the treatment or prevention of Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD) or schizophrenia, or at least one of the symptoms and/or syndromes thereof, or for cognition enhancement.

The present invention also relates to pharmaceutical composition comprising the compound of formula (I), as defined above for use in the treatment or prevention of diseases related to the $GABA_A$ α5 receptor, or for cognition enhancement.

The present invention also relates to pharmaceutical composition comprising the compound of formula (I), as defined above with one or more other active ingredients for use in the treatment or prevention of diseases related to the $GABA_A$ α5 receptor, or for cognition enhancement.

The term "treatment" refers to the alleviation of a specific pathological condition, the elimination or reduction of one or more of the symptoms of the condition, the slowing or elimination of the progression of the disease state, and the prevention or delay of recurrency of the pathological condition of a patient or subject already suffering from or diagnosed with the disease. The "prevention" (or prophylaxis or delay of action of the disease) is typically performed by administering the drug in the same or similar way as if it were given to a patient with a disease or condition already developed.

The term "therapeutically effective amount" refers to the amount of active ingredient—in comparison with the corresponding subject who did not receive such amount—which results in the treatment, cure, prevention or improvement of the disease or disease state or side effect, and reduces the progression of the disease or pathological condition. The term also includes effective amounts to enhance normal physiological function. For use in therapy the compound of formula (I), as defined above as well as any pharmaceutically acceptable salt thereof may be administered in a therapeutically effective amount as a raw chemical. In addition, the active ingredient is available as a pharmaceutical formulation. The exact therapeutically effective amount of the compound of formula (I), as defined above depends on a number of factors including, but not limited to, the age and body weight of the subject (patient), the precise type of disease requiring treatment and its seriousness, the nature of the medicinal product and the route of administration.

The term "subject" refers to a vertebrate. In certain embodiments, the vertebrate is a mammal. Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In one embodiment, the present invention relates to compounds of formula (I')

(I')

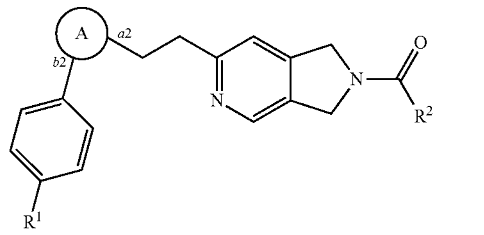

wherein

A is represented by

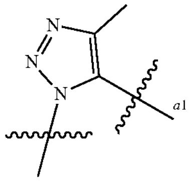
group,
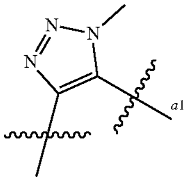
group, or
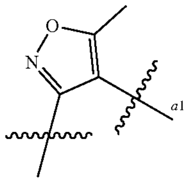
group, wherein site "a1" of any ring A is attached to site "a2" and wherein site "b1" of any ring A is attached to site "b2"

$R^1$ and $R^2$ are as defined above for the compounds of formula (I).

In one embodiment, the present invention relates to compounds of formula (I-a)

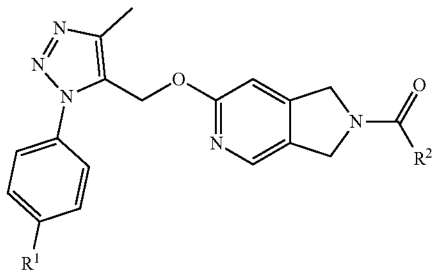

wherein $R^1$ is hydrogen or halogen, $R^2$ is $C_{1-4}$alkyl group, and/or salts thereof and/or biologically active metabolites thereof and/or prodrugs thereof and/or solvates thereof and/or hydrates thereof and/or polymorphs thereof.

In one embodiment, the present invention relates to compounds of formula (I-b)

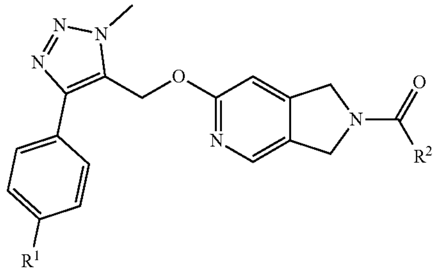

wherein $R^1$ is hydrogen or halogen, $R^2$ is $C_{1-4}$alkyl group, and/or salts thereof and/or biologically active metabolites thereof and/or prodrugs thereof and/or solvates thereof and/or hydrates thereof and/or polymorphs thereof.

In one embodiment, the present invention relates to compounds of formula (I-c)

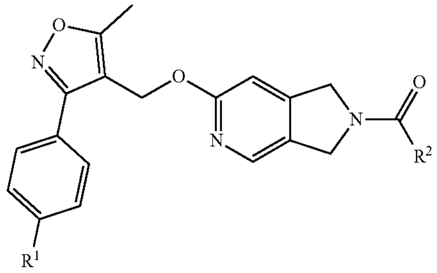

wherein $R^1$ is hydrogen or halogen, $R^2$ is $C_{1-4}$alkyl group, and/or salts thereof and/or biologically active metabolites thereof and/or prodrugs thereof and/or solvates thereof and/or hydrates thereof and/or polymorphs thereof.

In one embodiment, the present invention relates to compounds of formula (I) wherein $R^1$ is hydrogen.

In one embodiment, the present invention relates to compounds of formula (I) wherein $R^1$ is halogen.

In one embodiment, the present invention relates to compounds of formula (I) wherein $R^1$ is fluorine, chlorine or bromine.

In one embodiment, the present invention relates to compounds of formula (I) wherein $R^2$ is $C_{1-3}$alkyl.

In one embodiment, the present invention relates to compounds of formula (I) wherein $R^2$ is $C_{1-2}$alkyl.

In one embodiment, the present invention relates to compounds of formula (I) wherein $R^1$ is fluorine, bromine or chlorine and $R^2$ is $C_{1-3}$alkyl group.

In one embodiment, the present invention relates to compounds of formula (I) wherein $R^1$ is fluorine and $R^2$ is $C_{1-2}$alkyl group.

Any combination of the embodiments of A, $R^1$ and $R^2$ as defined above are preferred groups of compounds of formula (I).

In one embodiment, the present invention relates to compounds of formula (I), as defined above selected from the group consisting of:

1-(6-{[1-(4-fluorophenyl)-4-methyl-1H-1,2,3-triazol-5-yl]methoxy}-1,3-dihydro-2H-pyrrolo[3,4-c]pyridin-2-yl)ethanone, 1-(6-{[4-(4-fluorophenyl)-1-methyl-1H-1,2,3-triazol-5-yl]methoxy}-1,3-dihydro-2H-pyrrolo[3,4-c]pyridin-2-yl)ethanone, and 1-(6-{[3-(4-fluorophenyl)-5-methyl-1,2-oxazol-4-yl]methoxy}-1,3-dihydro-2H-pyrrolo[3,4-c]pyridin-2-yl)ethanone.

In describing the general synthesis of the compounds of formula (I), the biological assays and Examples, the following abbreviations have been used:

DCM=dichloromethane

DMSO=dimethyl sulfoxide

TLC=thin layer chromatography

The present invention also relates to a process for the preparation of compounds of formula (I) as defined above, comprising:

a) reacting a compound of formula (IV) with a compound of formula (V), to give a compound of formula (II), wherein $R^2$ is as defined above

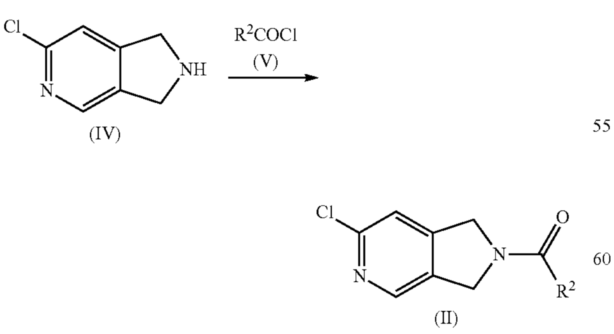

(IV)
(II)

b) reacting a compound of formula (II) with a compound of formula (III), to give a compound of formula (I), wherein $R^1$ and $R^2$ are as defined above

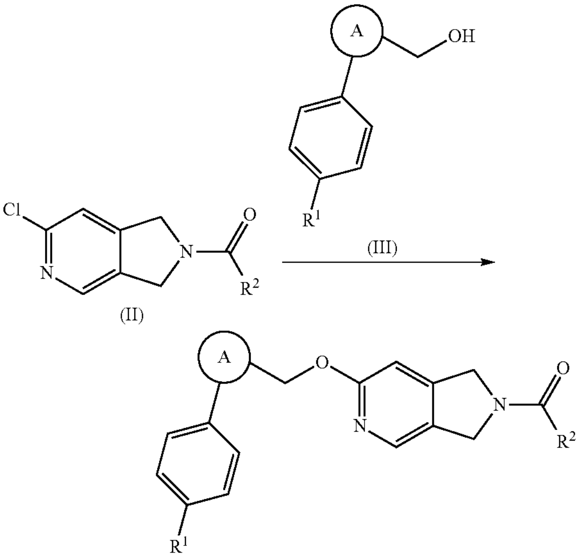

(II)
(I)

in particular:

b1) reacting a compound of formula (II) with a compound of formula (III-a), to give a compound of formula (I-a), wherein $R^1$ and $R^2$ are as defined above, or

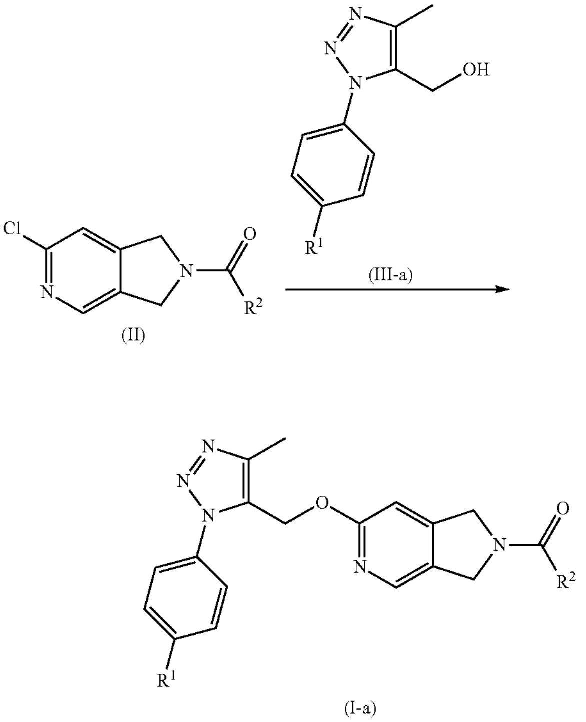

(II)
(I-a)

b2) reacting a compound of formula (II) with a compound of formula (III-b), to give a compound of formula (I-b), wherein $R^1$ and $R^2$ are as defined above, or

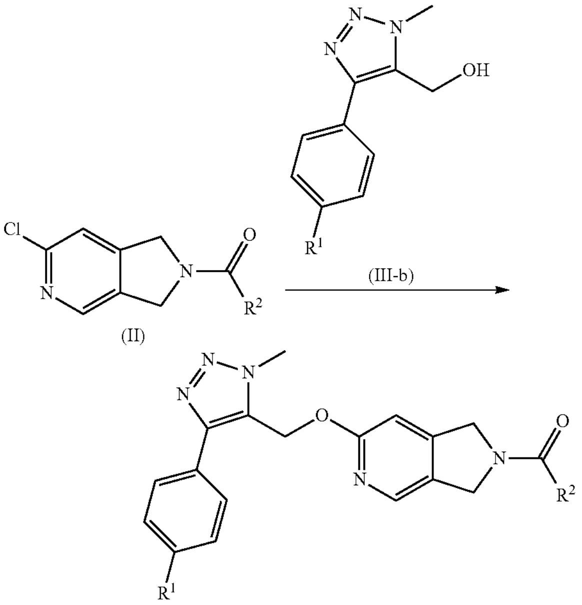

(II)

(I-b)

b3) reacting a compound of formula (II) with a compound of formula (III-c), to give a compound of formula (I-c), wherein $R^1$ and $R^2$ are as defined above

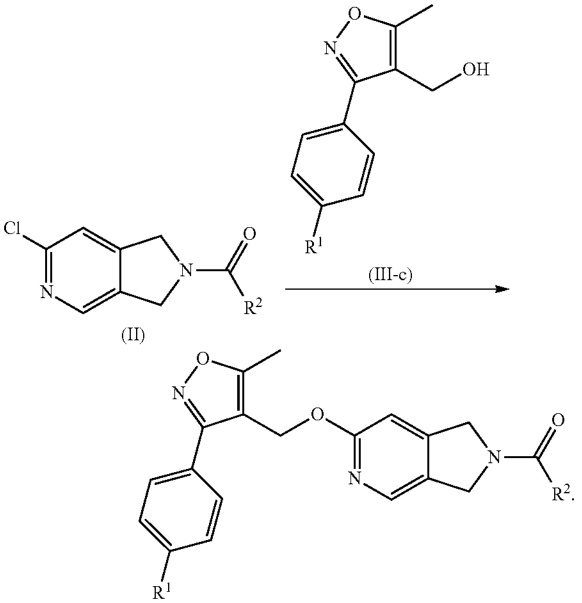

(II)

(I-c)

According to step a), acylation of commercially available bicyclic amine derivatives of formula (IV) with $R^2COCl$ of formula (V) in the presence of a base ($Et_3N$) provides the amide derivatives of formula (II).

In an aspect, the present invention provides novel intermediates of formula (II) synthesised in the process for preparing the compound of general formula (I) wherein R is as defined above for formula (I), preferably $C_{1-3}$alkyl group, more preferably $C_{1-2}$alkyl group, most preferably 1-(6-chloro-1,3-dihydro-2H-pyrrolo[3,4-c]pyridin-2-yl)ethanone.

The compounds of formula (I-a) wherein $R^1$ and $R^2$ are as defined in any of the embodiments described above can be prepared according to Scheme 1.

Scheme 1

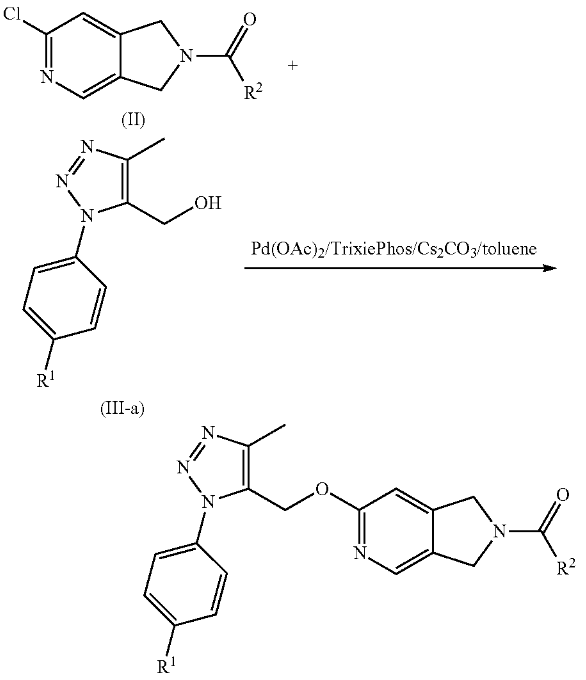

(II)

(III-a)

(I-a)

According to Scheme 1, etherification between amide derivatives of formula (II) and hydroxy derivatives of formula (III-a) can be carried out by a palladium-mediated process in the presence of a base ($Cs_2CO_3$) to provide a compound of formula (I-a). Hydroxy derivatives of formula (III-a) are known in the art (e.g. EP 0 433 842 A2, WO 2012/062623 A1) or can be synthesized by conventional methods.

The compounds of formula (I-b) wherein $R^1$ and $R^2$ are as defined in any of the embodiments described above can be prepared according to Scheme 2.

Scheme 2

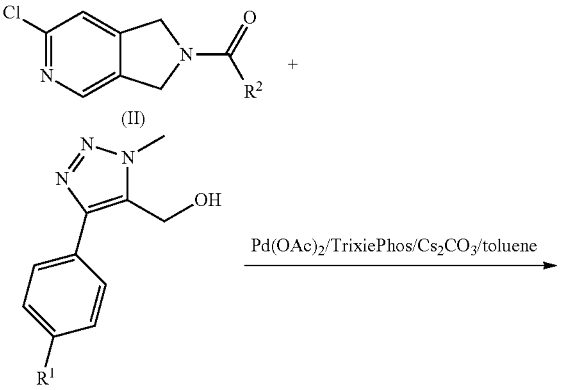

(II)

(III-b)

-continued

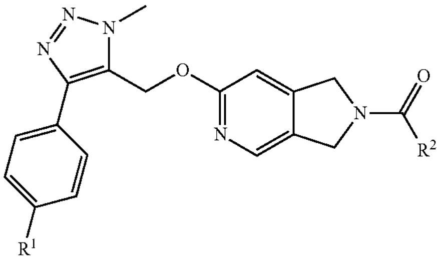

(I-b)

According to Scheme 2, etherification between amide derivatives of formula (II) and hydroxy derivatives of formula (III-b) can be carried out by a palladium-mediated process in the presence of a base ($Cs_2CO_3$) to provide a compound of formula (I-b). Hydroxy derivatives of formula (III-b) are known in the art (e.g. WO 2012/062687 A1) or can be synthesized by conventional methods.

The compounds of formula (I-c) wherein $R^1$ and $R^2$ are as defined in any of the embodiments described above can be prepared according to Scheme 3.

Scheme 3

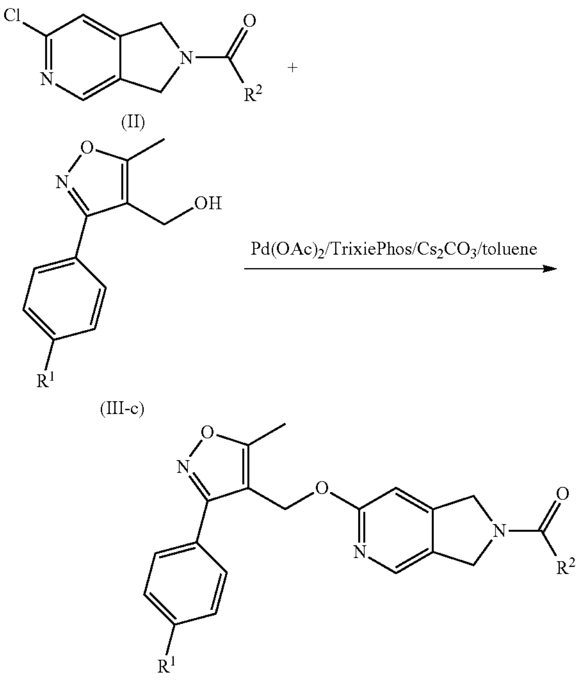

(II)

(III-c)

(I-c)

According to Scheme 3, etherification between amide derivatives of formula (II) and hydroxy derivatives of formula (III-c) can be carried out by a palladium-mediated process in the presence of a base ($Cs_2CO_3$) to provide a compound of formula (I-c). Hydroxy derivatives of formula (III-c) are known in the art (e.g. WO 2009/071476 A1 or WO 2013/057123 A1) or can be synthesized by conventional methods.

The reagents and detailed process steps required for the above reactions are set forth in the Examples.

The activity data of each of the compounds of formula (I) of the present invention are determined in vitro by the methods described below.

Biological Example 1: Binding Assay

The $GABA_A$ α5β3γ2 protein used for the receptor binding assay was derived from membranes produced from HEK cells (Millipore CYL3073) expressing the human recombinant $GABA_A$ α5β3γ2 receptor. Cells were stored and cultured in-house according to the instructions provided by the vendor (Millipor). Cell pellet was homogenized in 10 times modified Krebs Henseleit buffer (membrane preparation buffer): 20 mM Tris, 120 mM NaCl, 100 mM KCl, 25 mM $CaCl_2$ and 25 mM $MgCl_2$ pH=7.4 at 4° C. using Ultra Turrax (Janke&Kunkel) maximal speed for 15 seconds. The homogenate was centrifuged at 40,000 g for 30 minutes at 4° C. Supernatant was discarded and the resulting pellet was washed in membrane preparation buffer. Pellet was resuspended in membrane preparation buffer and aliquots of 1.4 mL ampulles were stored at −70° C. until use.

Receptor binding assays were performed in 96-well format in deep-well plates. For each 96-well plate one ampulle of membrane homogenate was thawed and diluted in binding buffer (50 mM Tris pH=7.4, 100 mM KCl) and 200 μL was dispensed into each well. Radioligand [$^3$H]Ro151788 (Perkin Elmer: NET757250UC) was prepared in binding buffer and added to each well in 50 μL volume to give final concentration of 0.5 nM. Test compounds in suitable concentration(s) were added in additional 50 μL. The final assay volume was 300 μL. Incubation was carried out for 60 minutes at 4° C. For non-specific binding 10 μM unlabeled diazepam was used. After incubation samples were filtered over UniFilter*GF/B™ using Filtermate Harvester (Perkin Elmer) and washed with 5×1 mL binding buffer. The plate was dried at 40° C. for an hour and 40 μL Microscint (Perkin Elmer) scintillation cocktail was added to each well. The plate was read in Microbeta (Perkin Elmer).

The specific radioligand binding (SB) was defined as the difference between total binding (Tot) and the non-specific binding (NSB). Results are expressed as a percent inhibition of specific binding obtained in the presence of compound of interest.

For $IC_{50}$ and $K_i$ determination a minimum of six drug concentrations in triplicate were used. $IC_{50}$ values (i.e. concentration of compound giving 50% inhibition of specific binding) were calculated from concentration-displacement curves by sigmoidal fitting using Origin 7.5 software. $K_i$ values (i.e. inhibition constants) were calculated using the Cheng-Prusoff equation $K_i = IC_{50}/[1+(L/K_D)]$, where [L] is the radioligand concentration and $K_D$ the affinity of the labelled ligand for receptor. $K_D$ was determined from the Saturation analyses.

The compounds of the present invention were tested in the above described assay, and all were found to have high affinity for the $GABA_A$ α5 receptor ($K_i$<50 nM).

Table 1 showing representative $hGABA_A$ α5 $K_i$ test results, obtained by the above described binding assay:

| Ex. | $hGABA_A$ α5 $K_i$ (nM) |
|---|---|
| 1 | 10 |
| 2 | 32 |
| 3 | 0.9 |

Biological Example 2: Functional Assay

Human HEK293 cell lines expressing $GABA_A$ α1β3γ2 and $GABA_A$ α5β3γ2 receptors were used in functional assays using the QPatch automated patch clamp system.

HEK293 cell lines stably expressing human recombinant $GABA_A$ α1β3γ2 receptor subunits (Millipore, CYL3073) or human recombinant $GABA_A$ α5β3γ2 receptor subunits (Millipore, CYL3053) were cultured in DMEM supplemented with 10% FBS (Gibco), passed two times per week and plated on Petri dishes previously coated with poly-d-lysine.

Automated whole-cell patch clamp recordings were made from cells 2-4 days after plating. Cells were detached using trypsin/EDTA (Sigma) treatment (2 minutes in 0.25% trypsin at 37° C.), then, after centrifugation (125G, 3 min, 2×), resuspended in a serum-free based media (Gibco, CHO-S-SFM-II) containing 12.5 mM HEPES, 1×penicillin-streptomycin-amphotericin (SigmaMix) and soybean trypsin inhibitor (Sigma, 0.04 mg/ml).

Cell suspension, as well as the extracellular solution (130 mM NaCl, 5 mM KCl, 5.1 mM HEPES, 4.9 mM HEPES-Na, 10 mM $CaCl_2$), 2 mM $MgCl_2$, 10 mM glucose and 0.1% DMSO, pH=7.35-7.4) and the intracellular solution (80 mM KCl, 50 mM KF, 36 mM KOH, 10 mM EGTA, 10 mM HEPES, 1.75 mM $MgCl_2$, 0.5 mM $CaCl_2$), 4 mM $Na_2ATP$. 14 mM phosphocreatine, 50 U/ml creatine-phosphokinase, 0.3 mM GTP, pH=7.25-7.3) were added to the QPatch-HTX automated patch clamp system (Sophion) in single-cell mode at room temperature. Inward currents were evoked at a holding potential of −80 mV by 3-s-long applications of the control agonist GABA at sub-maximal effective concentration (1 μM) at 2-4-min intervals first in concentration-matched DMSO (0.1 or 0.3%) control solution for five times, then in the presence of the test compound for four times, finally in control solution again for three times (wash-out). At the end of the experiment 100 μM GABA was applied to saturate the GABA-response and to assess the efficacy of the control GABA application. Current signals were low-pass filtered at 100 Hz and recorded at a sampling rate of 1 kHz.

The percentage modulation was calculated from the comparison of GAB A-evoked peak current amplitudes in the presence and absence of the test compound.

The compounds of the present invention were tested at 10 μM in the above described assay, and all were found to possess $GABA_A$ α5 negative allosteric modulator activity and selectivity for the α5 subtype over the α1. Preferred compounds have a functional efficacy at the α5 subtype of less than −30%.

Table 2 showing representative $hGABA_A$ α5 and $hGABA_A$ α1 functional efficacy test results obtained by the above described assay:

| Ex. | $hGABA_A$ α5 efficacy (%) | $hGABA_A$ α1 efficacy (%) |
|---|---|---|
| 1 | −43 | −2 |
| 2 | −47 | −6 |
| 3 | −44 | 13 |

The present invention will be further illustrated by the following Examples without limiting the scope of the present invention to them. From the above description and from the Examples, the person skilled in the art may ascertain the essential features of the invention and without departing from its essence and scope, may make certain changes and modifications in order to adapt the invention to various applications and conditions. As a result, the invention is not limited to the following illustrative examples, but rather to the scope determined by the appended claims.

In general, the compounds of formula (I) can be prepared according to the common general knowledge of the person skilled in the art and/or the methods described for the working examples. Solvents, temperatures, pressures and other reaction conditions can be easily selected by the person skilled in the art. Starting materials, such as the compounds of formulae (IV) and (V) are commercially available and/or can be easily prepared by the person skilled in the art according to literature procedure. During the preparation of compounds combinatorial techniques can be used, for example, where intermediates are suitable for the use of these methods.

Example 1

1-(6-{[1-(4-fluorophenyl)-4-methyl-1H-1,2,3-triazol-5-yl]methoxy}-1,3-dihydro-2H-pyrrolo[3,4-c]pyridin-2-yl)ethanone

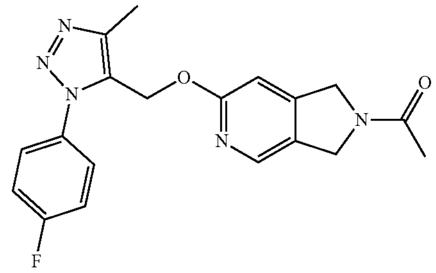 [SMILES: CC(=O)N1Cc2cnc(OCc3c(C)nnn3-c3ccc(F)cc3)cc2C1]

a.: 1-(6-chloro-1,3-dihydro-2H-pyrrolo[3,4-c]pyridin-2-yl)ethanone 600 mg (3.14 mmol) of 6-chloro-2,3-dihydro-1H-pyrrolo[3,4-c]pyridine hydrochloride was dissolved in 10 mL of anhydrous dichloromethane. 1905 mg (2.62 mL, 18.84 mmol) of anhydrous triethyl amine was added in one portion to the solution, and the reaction mixture was cooled with an ice-water bath. A solution of 259 mg (0.234 mL, 3.30 mmol) of acetyl chloride in 10 mL of anhydrous dichloromethane was added dropwise to the stirred reaction mixture during 10 minutes. The cooling bath was removed, and the mixture was allowed to warm up to room temperature. The conversion was checked by TLC (DCM:MeOH=95:5 as eluent, silica plate). The reaction mixture was washed with saturated sodium hydrogen carbonate solution and with water, dried over anhydrous sodium sulfate, and evaporated. Yield: 513 mg (83%), white solid identical to the title compound. MS (ESI) m/z: 197.0 $[M+H]^+$.

b.: 1-(6-{[1-(4-fluorophenyl)-4-methyl-1H-1,2,3-triazol-5-yl]methoxy}-1,3-dihydro-2H-pyrrolo[3,4-c]pyridin-2-yl)ethanone Under argon atmosphere a flask was charged with 99.5 mg (0.506 mmol) of 1-(6-chloro-1,3-dihydro-2H-pyrrolo[3,4-c]pyridin-2-yl)ethanone (step a.), 104 mg (0.502 mmol) of [4-(4-fluorophenyl)-1-methyl-1H-1,2,3-triazol-5-yl]methanol (WO 2012/062623 A1), 327 mg (1.000 mmol) of $Cs_2CO_3$, 20 mg (0.0502 mmol) of rac-2-(di-tert-butylphosphino)-1,11-binaphthyl, 10.1 mg (0.0452 mmol) of $Pd(OAc)_2$ and 4 mL of anhydrous toluene. The mixture was stirred at 90° C. for 16 hours. The conversion was checked by TLC (cyclohexane:acetone=1:2 as eluent, silica plate). The reaction mixture was filtered through a celite pad, washed with acetone, dried over anhydrous sodium sulfate, and evaporated. 215 mg residue was obtained, which was purified by flash column chromatography (silica gel, eluent: cyclohexane:acetone=1:2). Yield: 148 mg (80%), white, amorphous solid identical to the title compound. MS (ESI) m/z: 368.1 $[M+H]^+$.

Example 2

1-(6-{[4-(4-fluorophenyl)-1-methyl-1H-1,2,3-triazol-5-yl]methoxy}-1,3-dihydro-2H-pyrrolo[3,4-c]pyridin-2-yl)ethanone

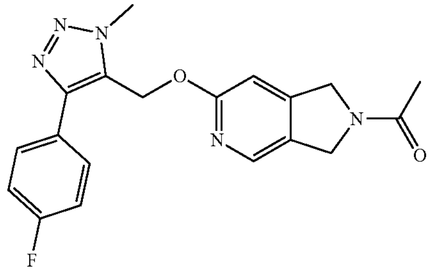 [SMILES: CC(=O)N1Cc2cnc(OCc3c(-c4ccc(F)cc4)nnn3C)cc2C1]

Under argon atmosphere a flask was charged with 99.5 mg (0.506 mmol) of 1-(6-chloro-1,3-dihydro-2H-pyrrolo[3,4-c]pyridin-2-yl)ethanone (step a. of Example 1), 104 mg (0.502 mmol) of [4-(4-fluorophenyl)-1-methyl-1H-1,2,3-triazol-5-yl]methanol (WO 2012/062687 A1), 327 mg (1.000 mmol) of $Cs_2CO_3$, 20 mg (0.0502 mmol) of rac-2-(di-tert-butylphosphino)-1,11-binaphthyl, 10.1 mg (0.0452 mmol) of $Pd(OAc)_2$ and 4 mL of anhydrous toluene. The mixture was stirred at 90° C. for 16 hours. The conversion was checked by TLC (cyclohexane:acetone=1:2 as eluent, silica plate). The reaction mixture was filtered through a celite pad, washed with acetone, dried over anhydrous sodium sulfate, and evaporated. 215 mg residue was obtained, which was purified by flash column chromatography (silica gel, eluent: cyclohexane:acetone=1:2). Yield: 43.8 mg (35.5%), white amorphous solid identical to the title compound. MS (ESI) m/z: 368.1 $[M+H]^+$.

Example 3

1-(6-{[3-(4-fluorophenyl)-5-methyl-1,2-oxazol-4-yl]methoxy}-1,3-dihydro-2H-pyrrolo[3,4-c]pyridin-2-yl)ethanone

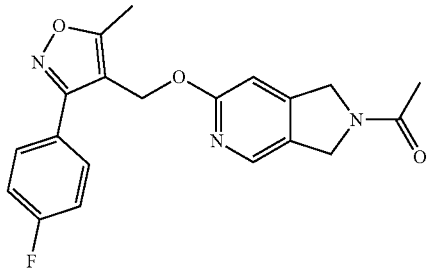 [SMILES: CC(=O)N1Cc2cnc(OCc3c(-c4ccc(F)cc4)noc3C)cc2C1]

Under argon atmosphere a flask was charged with 99.5 mg (0.506 mmol) of 1-(6-chloro-1,3-dihydro-2H-pyrrolo[3,4-c]pyridin-2-yl)ethanone (step a. of Example 1), 104 mg (0.502 mmol) of [3-(4-fluorophenyl)-5-methyl-1,2-oxazol-4-yl]methanol (WO 2009/071476 A1), 327 mg (1.000 mmol) of $Cs_2CO_3$, 20 mg (0.0502 mmol) of rac-2-(di-tert-butylphosphino)-1,11-binaphthyl, 10.1 mg (0.0452 mmol) of $Pd(OAc)_2$ and 4 mL of anhydrous toluene. The mixture was stirred at 90° C. for 16 hours. The conversion was checked by TLC (cyclohexane:acetone=1:2 as eluent, silica plate). The reaction mixture was filtered through a celite pad, washed with acetone, dried over anhydrous sodium sulfate, and evaporated. 215 mg residue was obtained, which was purified by flash column chromatography (silica gel, eluent: cyclohexane:acetone=1:2). Yield: 24 mg (13%), white amorphous solid identical to the title compound. MS (ESI) m/z: 368.1 $[M+H]^+$.

Pharmaceutical Preparation Examples

The following formulation examples illustrate representative pharmaceutical compositions of this invention. The present invention however is not limited to the following pharmaceutical compositions.

A) Solid Oral Dosage Forms

| I., Tablets | |
|---|---|
| Active ingredient(s) | 0.01-90% |
| Filler | 1-99.9% |
| Binder | 0-20% |
| Disintegrant | 0-20% |
| Lubricant | 0-10% |
| Other specific excipient(s) | 0-50% |

| II., Orodispersible films | |
|---|---|
| Active ingredient(s) | 0.01-90% |
| Film forming agent | 1-99.9% |
| Plasticizer | 0-40% |
| Other specific excipient(s) | 0-50% |

B) Liquid Oral Dosage Forms

| III., Oral suspensions | |
|---|---|
| Active ingredient(s) | 0.01-50% |
| Liquid vehicle | 10-99.9% |
| Wetting agent | 0-50% |
| Thickener | 0-50% |
| Buffering agent | q.s. |
| Osmotic agent | 0-50% |
| Preservatives | q.s. |

| IV., Syrups | |
|---|---|
| Active ingredient(s) | 0.01-50% |
| Solvent | 10-99.9% |
| Sugar component | 1-20% |
| Flavouring agents | 0-10% |

C) Parenteral Dosage Forms

| V., Intravenous injections | |
|---|---|
| Active ingredient(s) | 0.01-50% |
| Solvent | 10-99.9% |
| Co-solvent | 0-99.9% |
| Osmotic agent | 0-50% |
| Buffering agent | q.s. |

D) Other Dosage Forms

| VI., Suppositories | |
|---|---|
| Active ingredient(s) | 0.01-50% |
| Suppository base | 1-99.9% |
| Surface-active agents | 0-20% |
| Lubricants | 0-20% |
| Preservatives | q.s. |

| VII., Eye drops | |
|---|---|
| Active ingredient(s) | 0.01-50% |
| Water | 0-99.9% |
| Solvent | 0-99.9% |
| Osmotic agent | 0-20% |
| Viscosity enhancer | 0-20% |
| Bufferin agent | q.s. |
| Preservatives | q.s. |

| VIII., Nasal drops or spray | |
|---|---|
| Active ingredient(s) | 0.01-50% |
| Water | 0-99.9% |
| Solvent | 0-99.9% |
| Osmotic agent | 0-20% |
| Viscosity enhancer | 0-20% |
| Co-solvent | q.s. |
| Bufferin agent | q.s. |
| Preservatives | q.s. |

The invention claimed is:

1. A compound of formula (I)

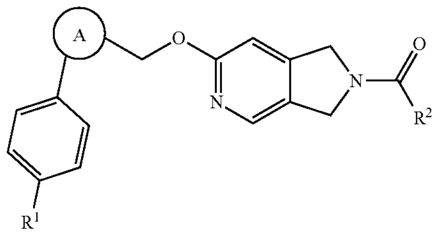

(I)

wherein

A is represented by a

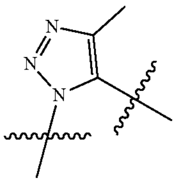

group,

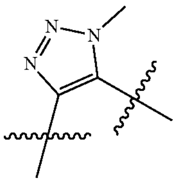

group, or

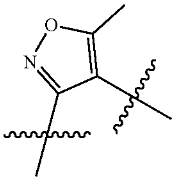

group, $R^1$ is hydrogen or halogen, and $R^2$ is a $C_{1-4}$alkyl group, or pharmaceutically acceptable salts thereof.

2. The compound according to claim 1, having formula (I-a)

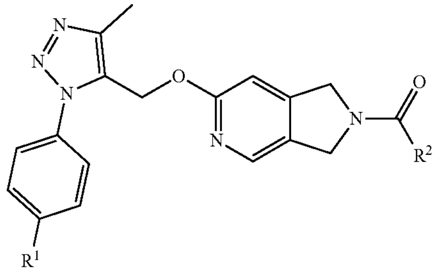

(I-a)

wherein $R^1$ is hydrogen or halogen, and $R^2$ is a $C_{1-4}$alkyl group.

3. The compound according to claim 1, having formula (I-b)

(I-b)

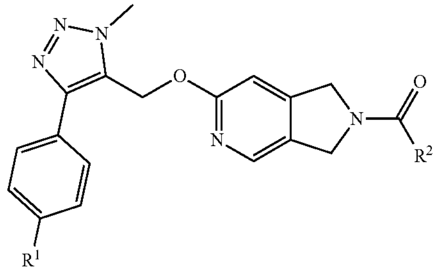

wherein $R^1$ is hydrogen or halogen, and $R^2$ is a $C_{1-4}$alkyl group.

4. The compound according to claim 1, having formula (I-c)

(I-c)

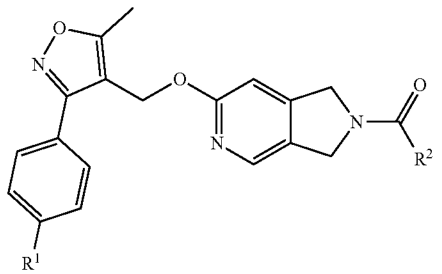

wherein $R^1$ is hydrogen or halogen, and $R^2$ is a $C_{1-4}$alkyl group.

5. The compound according to claim 1, wherein $R^1$ is halogen and $R^2$ is a $C_{1-4}$alkyl group.

6. The compound according to claim 1, wherein $R^1$ is fluorine, bromine or chlorine, and $R^2$ is a $C_{1-3}$alkyl group.

7. The compound according to claim 1, wherein $R^1$ is fluorine, and $R^2$ is a $C_{1-2}$alkyl group.

8. The compound according to claim 1 selected from the group consisting of 1-(6-{[1-(4-fluorophenyl)-4-methyl-1H-1,2,3-triazol-5-yl]methoxy}-1,3-dihydro-2H-pyrrolo[3,4-c]pyridin-2-yl)ethanone, 1-(6-{[4-(4-fluorophenyl)-1-methyl-1H-1,2,3-triazol-5-yl]methoxy}-1,3-dihydro-2H-pyrrolo[3,4-c]pyridin-2-yl)ethanone, and 1-(6-{[3-(4-fluorophenyl)-5-methyl-1,2-oxazol-4-yl]methoxy}-1,3-dihydro-2H-pyrrolo[3,4-c]pyridin-2-yl)ethanone.

9. A method of treating a disease related to the $GABA_A$ α5 receptor, or for cognition enhancement, comprising administering to a subject in need of such treatment an effective amount of at least one compound according to claim 1.

10. The method according to claim 9, wherein the disease related to the $GABA_A$ α5 receptor is selected from the group consisting of neurodegenerative disorders, neurocognitive disorders, neurodevelopmental disorders, schizophrenia, mood disorders, pain disorders, and substance-related and addictive disorders.

11. The method according to claim 9, wherein the disease related to the $GABA_A$ α5 receptor is selected from the group consisting of Alzheimer's disease (AD), cognition deficiency disorders, memory deficits, age-associated memory impairment or cognitive decline, dementia, mild cognitive impairment (MCI), vascular cognitive impairment (VCI), CNS conditions occurring after stroke, cognitive impairment associated with brain cancers, cognitive decline in Down Syndrome (DS), cognitive dysfunction in major depressive disorder (MDD), and schizophrenia.

12. A method of treating a disease related to the $GABA_A$ α5 receptor, or for cognition enhancement, comprising administering to a subject in need of such treatment an effective amount of at least one compound according to claim 1 in combination with one or more other active ingredients.

13. A pharmaceutical composition comprising at least one compound according to claim 1 and at least one pharmaceutically acceptable excipient.

14. The pharmaceutical composition according to claim 13, wherein the composition further comprises one or more other active ingredients.

15. A process for the preparation of a compound of formula (I) of claim 1, comprising a) reacting a compound of formula (IV) with a compound of formula (V) in the presence of a base, to give a compound of formula (II), wherein $R^2$ is as defined above

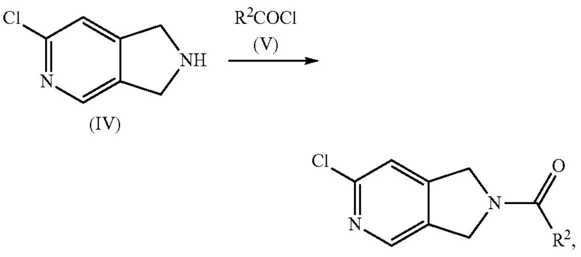

(IV)

(II)

b) reacting a compound of formula (II) with a compound of formula (III), wherein $R^1$ is as defined above in a palladium-mediated process in the presence of a base to provide a compound of formula (I)

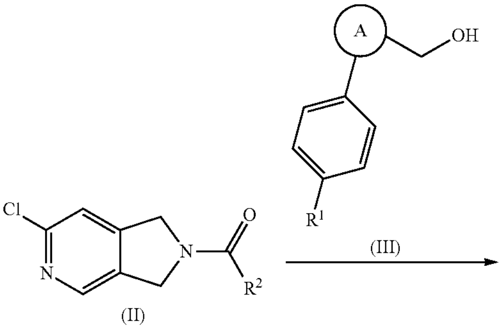

(II)

-continued
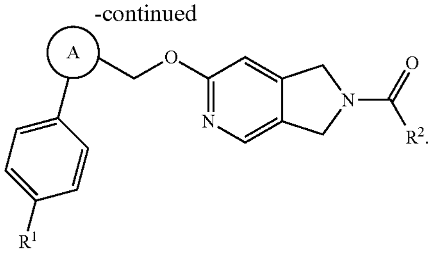
(I)
* * * * *